(12) United States Patent
Leibrandt

(10) Patent No.: US 12,232,836 B2
(45) Date of Patent: Feb. 25, 2025

(54) APPARATUS, SYSTEMS AND METHODS FOR DYNAMIC ONLINE KINEMATIC ADAPTATION OF MEDICAL ROBOTS

(71) Applicant: Auris Health, Inc., Redwood City, CA (US)

(72) Inventor: Konrad Leibrandt, Corona, CA (US)

(73) Assignee: Auris Health, Inc., Santa Clara, CA (US)

( * ) Notice: Subject to any disclaimer, the term of this patent is extended or adjusted under 35 U.S.C. 154(b) by 718 days.

(21) Appl. No.: 17/076,755

(22) Filed: Oct. 21, 2020

(65) Prior Publication Data

US 2021/0121253 A1 Apr. 29, 2021

Related U.S. Application Data

(60) Provisional application No. 62/924,905, filed on Oct. 23, 2019.

(51) Int. Cl.
| | | |
|---|---|---|
| *B25J 9/00* | (2006.01) | |
| *A61B 34/00* | (2016.01) | |
| *A61B 34/20* | (2016.01) | |
| *A61B 34/35* | (2016.01) | |
| *B25J 9/16* | (2006.01) | |

(52) U.S. Cl.
CPC .............. *A61B 34/35* (2016.02); *A61B 34/20* (2016.02); *A61B 34/74* (2016.02); *B25J 9/0072* (2013.01); *B25J 9/1682* (2013.01)

(58) Field of Classification Search
CPC ......... A61B 34/35; A61B 34/20; A61B 34/74; A61B 34/76; A61B 34/37; B25J 9/0072; B25J 9/1682; B25J 9/162; B25J 9/0087; B25J 9/1607; G05B 2219/39172
See application file for complete search history.

(56) References Cited

U.S. PATENT DOCUMENTS

| | | | | |
|---|---|---|---|---|
| 2009/0326324 A1* | 12/2009 | Munoz Martinez | ... | A61B 34/30 901/30 |
| 2012/0071895 A1* | 3/2012 | Stahler | ................... | A61B 34/20 606/130 |
| 2016/0113728 A1* | 4/2016 | Piron | ..................... | A61B 34/30 606/130 |

(Continued)

*Primary Examiner* — Khoi H Tran
*Assistant Examiner* — Tien Minh Le
(74) *Attorney, Agent, or Firm* — Paradice & Li LLP

(57) ABSTRACT

In a robotic medical system comprising a staging kinematic chain coupled to a plurality of independently articulable robotic arms capable of motion with one or more degrees of freedom, a first configuration of robotic arms may be determined based on a first inverse kinematic model including the robotic arms and assuming a static staging kinematic chain. The first configuration may effectuate desired poses of instruments coupled to the robotic arms. A set of control parameter values associated with the robotic arms may be determined based on the first configuration, and, when a determined control parameter value falls outside a corresponding control parameter range, a staging kinematic chain pose and a second configuration of the robotic arms to effectuate the desired poses of the instruments may be determined. The second configuration is determined using a second inverse kinematic model that includes the robotic arms and assumes a mobile staging kinematic chain.

19 Claims, 10 Drawing Sheets

(56) References Cited

U.S. PATENT DOCUMENTS

| | | | |
|---|---|---|---|
| 2019/0105117 A1* | 4/2019 | Brisson | A61B 34/30 |
| 2020/0261169 A1* | 8/2020 | Miller | B25J 9/1607 |
| 2022/0281100 A1* | 9/2022 | Brogardh | B25J 9/0057 |
| 2022/0287788 A1* | 9/2022 | Parastegari | A61B 34/77 |

* cited by examiner

APPARATUS, SYSTEMS AND METHODS FOR DYNAMIC ONLINE KINEMATIC ADAPTATION OF MEDICAL ROBOTS

CROSS-REFERENCE TO RELATED APPLICATIONS

This application claims the benefit of and priority to U.S. Provisional Patent Application No. 62/924,905, entitled, "APPARATUS, SYSTEMS AND METHODS FOR DYNAMIC ONLINE KINEMATIC ADAPTATION OF MEDICAL ROBOTS," filed Oct. 23, 2019, which is assigned to the assignee hereof, and incorporated by reference in its entirety, herein.

FIELD

The subject matter disclosed herein relates to robotic medical systems, devices, and methods for kinematically adapting medical robots to facilitate medical procedures.

BACKGROUND

Robotic medical systems are used during minimally invasive or non-invasive medical procedures such as imaging tissue, performing biopsies, surgery, or other medical procedures. In some systems, a robotic arm, which may include multiple sections linked by joints, may be used by an operator to manipulate a medical instrument coupled to the robotic arm during a medical procedure. Robotic arms may be attached to a common base, which may be immobile during performance of the medical procedure. In many instances, the medical procedures being performed can be hampered because the motion of one or more sections of a robotic arm may be constrained due to physical limitations. For example, one or more actuators may be at maximum extension and prevent arm motion in certain directions. In general, such physical constraints may distract or limit medical practitioners from the procedure being performed, lead to delays and/or inefficiencies to adjust or reposition robots, and/or impact patient safety because the medical practitioner may not have any a priori indication of motion limits of the robotic medical system until a specific procedure has already commenced.

Accordingly, some embodiments disclosed herein enhance safety and improve procedural efficiency, in part by facilitating instrument motion and control during medical procedures.

SUMMARY

In some embodiments, a method may be performed on a robotic medical system comprising a staging kinematic chain capable of motion with one or more degrees of freedom (DOF), wherein the staging kinematic chain is coupled to a plurality of independently articulable robotic arms. The method may comprise: determining a first configuration of the robotic arms based on a first inverse kinematic model that includes the robotic arms and assumes that the staging kinematic chain is static, wherein the first configuration of the robotic arms effectuates one or more corresponding desired poses of one or more instruments coupled to the robotic arms; determining a set of control parameter values associated with one or more of the robotic arms based on the first configuration; and determining, in response to at least one determined control parameter value falling outside a corresponding control parameter range, a pose of the staging kinematic chain and a second configuration of the robotic arms to effectuate the one or more corresponding desired poses of the one or more instruments, wherein the second configuration is determined based on a second inverse kinematic model that includes the robotic arms and assumes that the staging kinematic chain is mobile.

In a further aspect, a robotic medical system may comprise: a staging kinematic chain, capable of motion with one or more degrees of freedom (DOF), a plurality of independently articulable robotic arms coupled to the staging kinematic chain, one or more instruments coupled to the robotic arms, and a processor operationally coupled to the staging kinematic chain, the plurality of robotic arms, and the one or more instruments. The processor may be configured to: determine a first configuration of the robotic arms based on a first inverse kinematic model that includes the robotic arms and assumes that the staging kinematic chain is static, wherein the first configuration of the robotic arms effectuates one or more corresponding desired poses of the one or more instruments coupled to the robotic arms; determine a set of control parameter values associated with one or more of the robotic arms based on the first configuration; and determine, in response to at least one determined control parameter value falling outside a corresponding control parameter range, a pose of the staging kinematic chain and a second configuration of the robotic arms to effectuate the one or more corresponding desired poses of the one or more instruments, wherein the second configuration is determined based on a second inverse kinematic model that includes the robotic arms and assumes that the staging kinematic chain is mobile.

In another aspect, an apparatus may comprise staging kinematic chain means capable of motion with one or more degrees of freedom (DOF) and a plurality of independently articulable robotic arm means. The method may comprise: means for determining a first configuration of the robotic arm means based on a first inverse kinematic model that includes the robotic arm means and assumes that staging kinematic chain means is static, wherein the first configuration of the robotic arm means effectuates corresponding desired poses of instrument means; means for determining a set of control parameter values associated with the robotic arm means based on the first configuration; and means for determining, in response to at least one determined control parameter value falling outside a corresponding control parameter range, a pose of staging kinematic chain means and a second configuration of the robotic arm means to effectuate the corresponding desired poses of the instrument means based on a second inverse kinematic model that includes the robotic arms and assumes that the staging kinematic chain is mobile.

In some embodiments, a non-transitory computer-readable medium comprising instructions to configure a processor coupled to a robotic medical system to: determine a first configuration of the robotic arms based on a first inverse kinematic model that includes the robotic arms and assumes that the staging kinematic chain is static, wherein the first configuration of the robotic arms effectuates one or more corresponding desired poses of the one or more instruments coupled to the robotic arms; determine a set of control parameter values associated with one or more of the robotic arms based on the first configuration; and determine, in response to at least one determined control parameter value falling outside a corresponding control parameter range, a pose of the staging kinematic chain and a second configuration of the robotic arms to effectuate the one or more corresponding desired poses of the one or more instruments, wherein the second configuration is determined based on a second inverse kinematic model that includes the robotic arms and assumes that the staging kinematic chain is mobile.

The methods disclosed may be performed by one or more processors, and/or robotic medical devices, etc. The disclosed methods may be embodied on computer-readable media or computer-readable memory.

BRIEF DESCRIPTION OF THE DRAWINGS

Embodiments of the invention will be described, by way of example only, with reference to the drawings.

Figure 1A:
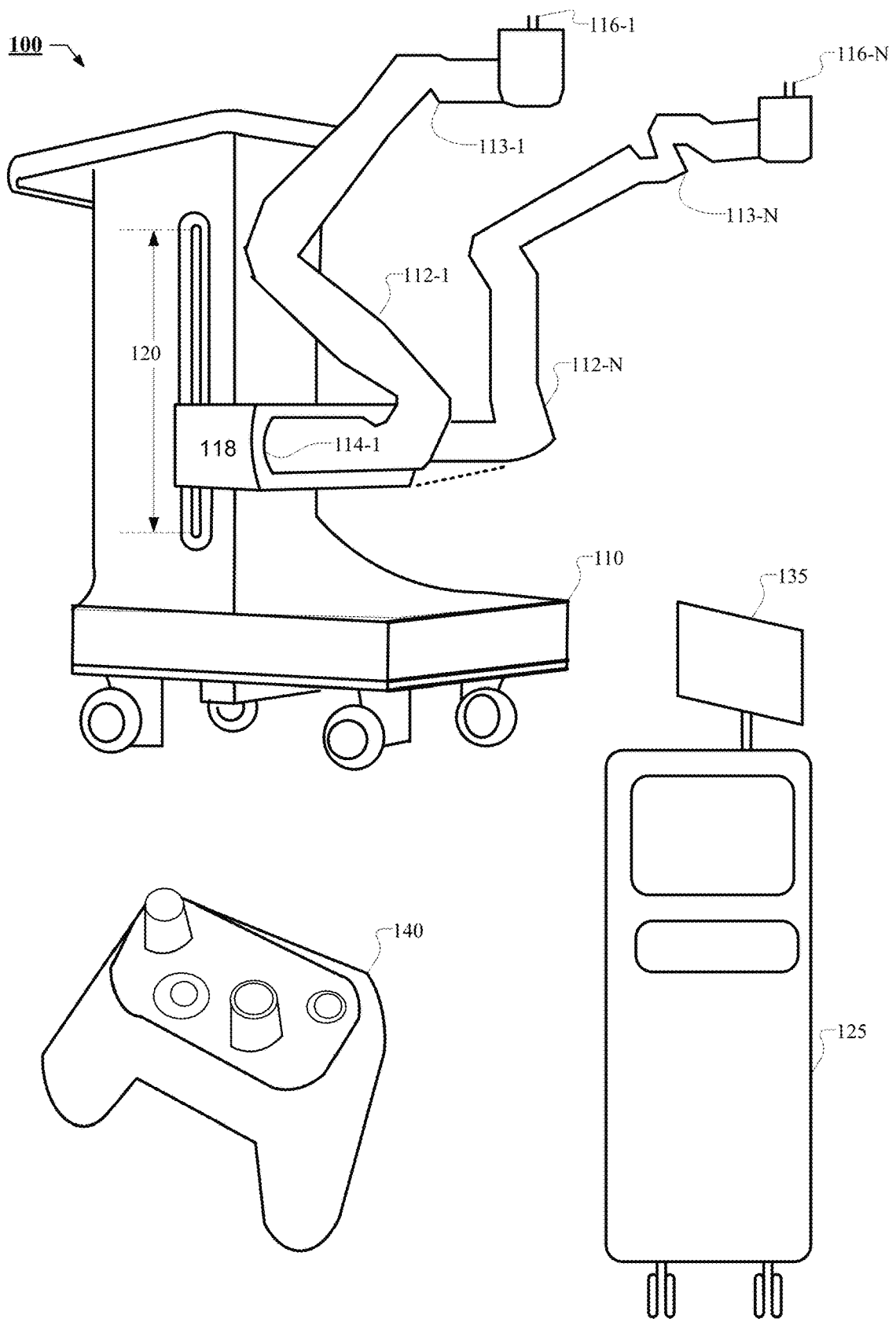
FIG. 1A shows an example diagram illustrating some components of an example robotic medical system in accordance with certain embodiments disclosed herein.

Like reference numbers and symbols in the various figures indicate like elements, in accordance with certain example embodiments. In addition, multiple instances of an element may be indicated by following a first number for the element with a letter or with a hyphen and a second number. For example, multiple instances of an element 112 may be indicated as 112-1, 112-2, 112-N etc. When referring to such an element using only the first number, any instance of the element is to be understood (e.g. element 112 in the previous example would refer to elements 112-1, 112-2, and/or 112-N).

DETAILED DESCRIPTION

Embodiments disclosed herein enhance safety and improve procedural efficiency, in part by facilitating instrument motion and control during medical procedures, including robot assisted medical procedures such as endoscopy, laparoscopy, and/or endolumenal procedures.

Robotic medical systems are increasingly used during minimally invasive or non-invasive medical procedures such as imaging tissue, performing biopsies, surgery, diagnostics, etc. The term "non-invasive" relates to the use of naturally occurring openings in the human body (e.g. mouth, nose, anus, urethral openings, etc.) to perform medical procedures. The term "minimally invasive" refers to the use of one or more small incisions (relative to incisions conventionally used for a procedure) to perform a medical procedure. These medical procedures may include gastrointestinal (GI) tract procedures, trans-oral procedures, colorectal procedures, urologic procedures, gynecological procedures, thoracic and/or pulmonary procedures, cardiac procedures, and various other types of surgical and/or diagnostic procedures.

Robotic medical systems may include devices that use one or more arms (also referred to herein as "robotic arms"), where each arm may include multiple sections linked by joints. On each arm, actuators coupled to joints and arm sections, may be used to move and reorient arm sections (or sub-arms) to effect a desired pose of one or more medical instruments coupled to a distal end of the arm. The instruments may be used to facilitate and/or perform medical procedures. A proximal end of each arm on the robotic medical system may be coupled to a base common to the arms. Conventionally, the base is immobilized during performance of the medical procedure. Further, the common base may be coupled to a platform, which may house electronics and other controls to power and operate the one or more arms and the base.

In many instances, medical procedures being performed can be hampered because the motion of one or more sections of a robotic arm may be constrained due to physical limitations. For example, one or more actuators on an arm may be at maximum extension and prevent arm motion in certain directions. In general, such physical constraints may: (a) distract or limit medical practitioners from the procedure being performed, (b) lead to delays and/or inefficiencies to adjust or reposition the platform and/or robotic arms, and/or (c) impact patient safety because the medical practitioner may not have any a priori indication of motion limits of the robotic medical system until a specific procedure has already commenced. For example, in a robotic medical system with multiple arms, repositioning a platform during a medical procedure may involve, among other actions, removal of all instruments from a patient's body, repositioning of the platform, repeating any set up procedures, re-navigating instruments to the prior locations within the patient's body—all prior to recommencing. Thus, the time taken for the medical procedure may be detrimentally impacted and/or operator cognitive load may increase significantly depending on the complexity of the above tasks. In addition, such distractions can lead to errors, affect patient safety or recovery time, increase procedure cost, and/or decrease medical practitioner availability for other patients/procedures. In sum, instrument motion and positioning constraints, which may occur because of actuator and/or joint limitations on an arm, can detrimentally affect the duration, performance, efficiency, cost, and safety of medical procedures performed using a robotic medical system.

In some embodiments, a robotic medical system may facilitate effectuation of instrument poses in response to an existing or predicted system state by facilitating motion of a staging kinematic chain in during a medical procedure in addition to movement of robotic arms. A kinematic chain may be viewed as an assembly of one or more rigid parts. The component parts may be connected by articulated joints. The pose of a kinematic chain may be determined from (or represented by) the pose(s) of each of its component parts. For example, the poses of individual parts of a kinematic chain along with joint articulation parameters may be used to determine the pose of a kinematic chain.

In some embodiments, a robotic medical system may comprise a staging kinematic chain (S) capable of motion with one or more degrees of freedom (DOF), wherein the staging kinematic chain (S) may be coupled to a proximal end of a plurality of independently articulable robotic arms $A=\{A_r|1\leq r\leq N, N\geq 2\}$, where $A_r$ is a robotic arm and N represents the number of robotic arms. Each robotic arm $A_r$ may be coupled, at its distal end, to one or more instruments (also referred to herein as "end effectors") $E_{k\_r}$, $1\leq k\leq M_r$, where $M_r$ is the number of instruments coupled to the distal end of robotic arm $A_r$. Further, each instrument $E_{k\_r}$ may be associated with a corresponding pose $P_{k\_r}$. The pose $P_{k\_r}$ of instrument $E_{k\_r}$ refers to the position and orientation of instrument $E_{k\_r}$ in task space.

Thus, for a robotic arm $A_r$, the set of instruments may be given by $E_r=\{E_{k\_r}|1\leq k\leq M_r\}$ and the corresponding poses by $P_r=\{P_{k\_r}|1\leq k\leq M_r\}$. Further, the set of instruments may be written as $E=\{E_r|1\leq r\leq N, N\geq 2\}$ with corresponding instrument poses written as $P=\{P_r|1\leq r\leq N, N\geq 2\}$.

In some embodiments (e.g. where $k=M_r=1$ for all r), each robotic arm $A_r$ may be coupled to a single distinct corresponding instrument, which may be written as $E_{k\_r}=E_{1\_r}=E_r$ and $E=\{E_r|1\leq r\leq N, N\geq 2\}$. Similarly, the pose associated with the corresponding instrument may be written as $P_{k\_r}=P_{1\_r}=P_r$ and $P=\{P_r|1\leq r\leq N, N\geq 2\}$. For illustrative purposes only, in the examples below, each robot arm $A_r$ is assumed to be coupled to a single distinct instrument $E_r$ with pose $P_r$ so that $E=\{E_r|1\leq r\leq N, N\geq 2\}$ and $P=\{P_r|1\leq r\leq N, N\geq 2\}$. However, it is understood that the apparatus and techniques disclosed may be applied when robot arms are coupled to more than one instrument.

In some embodiments, at a first time, a first corresponding configuration $C_1=\{C_{1\_r}|1\leq r\leq N\}$ of the robotic arms A may be determined to effectuate corresponding desired poses P of instruments E coupled to the robotic arms A, wherein the first corresponding configuration $C_1$ of the independent arms may be determined based on a first inverse kinematic model that includes the robotic arms and assumes that the staging kinematic chain (S) is static. For a given robotic arm $A_r$, the first corresponding robot arm configuration may written as $C_{1\_r}=\{c_{1r\_f}|1\leq f\leq F_r\}$, where $c_{1r\_f}$ represents the first configuration of joint f associated with robotic arm $A_r$ and $F_r$ represents the number of joints on robotic arm $A_r$. Each robotic arm $A_r$ may comprise one or more joints so that $1\leq f\leq F_r$. Thus, the pose $P_r$ of instrument $E_r$ coupled to the robotic arm $A_r$ may be determined by the configuration $C_{1\_r}$ of joints associated with the robotic arm $A_r$. The configuration $C_{1\_r}$ of a robotic arm (also referred to herein as joint configuration) refers to the position value of each joint associated with the robotic arm $A_r$ in joint space. Joint space is defined by a vector whose components are the translational and/or angular displacements of each joint of a robotic link relative to a (joint space) frame of reference. The configuration of a joint on the robotic arm $A_r$ may be determined by actuator states associated with each joint. Thus, when the staging kinematic chain is static, the configuration $C_{1\_r}$ of an arm $A_r$ may be determined by the configuration of joints on the arm. Accordingly, the joint configuration $C_{1\_r}$ (in joint space) may be represented as a vector of the actuator values (e.g. with one actuator value per actuator), The actuator values may include angular values.

Kinematic models use mathematical relationships between position, velocity, and acceleration for joints and/or robot arm sections to determine unknowns. Based on a kinematic model for the robotic medical system, actuator inputs may be determined to achieve actuator states that move, rotate, and/or place joints in the robotic arm and/or instruments (or end effectors) coupled to the robotic arm in appropriate (desired) poses. Forward kinematics determines the poses of instruments/end effectors coupled to a robot arm based on known joint configurations associated with the robotic arm. Inverse kinematics determines a configuration of a robot arm (or joint configurations for the robot arm) based on a known (or desired) poses of instruments/end effectors coupled to the robot arm.

A set of control parameter values $V=\{V_r|1\leq r\leq N\}$, associated with the robotic arms A may be determined based on the first corresponding configuration $C_1$, where, for each robotic arm $A_r$, the set of control parameter values $V_r$ may be written as $V_r=\{v_{rq}|1\leq q\leq Q_r\}$, where $Q_r$ is the number of control parameter values associated with robot arm $A_r$. In some embodiments, in response to the value of at least one determined control parameter $v_{rq}$ falling outside a corresponding control parameter range (e.g. $v_{rq}<T1$ or $v_{rq}>T2$), a configuration Cs (which may correspond to a pose $P_S$) of the staging kinematic chain and a second corresponding configuration of the robotic arms $C_2=\{C_{2\_r}|1\leq r\leq N\}$ to effectuate the corresponding desired poses P of instruments E may be determined, wherein the second corresponding configuration $C_2$ of the robotic arms A is determined based on a second inverse kinematic model that includes the robotic arms A and assumes a mobile staging kinematic chain S.

In some embodiments, the first inverse kinematic model may be used to determine the first corresponding configuration $C_1$ of the robotic arms A by determining, for each robotic arm $A_r$, corresponding actuator positions. For example, the configuration of arm $A_r$ may be determined by determining actuator positions (e.g. at various joints) associated with robotic arm $A_r$. In some embodiments, the corresponding actuator positions for each robotic arm $A_r$ may be determined independently of other robotic arms $A_u$, $u\neq r$ and independently of the staging kinematic chain (S). In some embodiments, the first inverse kinematic model may be based on N independent kinematic chains, wherein each kinematic chain corresponds to a robotic arm $A_r$ in the plurality of robotic arms A.

In some embodiments, at the first time, the second inverse kinematic model may be used to determine a second corresponding configuration $C_2$ of the robotic arms A based on: (i) the degrees of freedom (DoFs) available to the staging kinematic chain (S) and (ii) available DOFs to each independent arm $A_r$. In some embodiments, the second inverse kinematic model may be based on a single kinematic chain comprising the staging kinematic chain (S) and the plurality of robotic arms A.

In some embodiments, the switch from the first corresponding configuration of the robotic arms $C_1$ to the second corresponding configuration of the robotic arms $C_2$ at the first time, may be effectuated dynamically during a medical procedure. In some embodiments, the robotic medical system may dynamically switch between the first inverse kinematic model and the second inverse kinematic model. For example, the robotic medical system may dynamically switch to the first inverse kinematic model upon effectuation of the corresponding desired poses $P_{k\_r}$ of instruments $E_{k\_r}$ coupled to the robotic arms A based on the second inverse kinematic model. For example, once the corresponding desired poses of instruments $P_{k\_r}$ of instruments $E_{k\_r}$ coupled to the robotic arms A have been effectuated (based on the second inverse kinematic model), the robotic medical system may dynamically switch to the first inverse kinematic model.

In some embodiments, the dynamic switch between the first inverse kinematic model to the second inverse kinematic model (or vice versa) may occur within a control tick. In some embodiments, corresponding desired poses $P_{k\_r}$ of instruments $E_{k\_r}$ coupled to the robotic arms A (e.g. as determined by the first inverse kinematic model or the second inverse kinematic model) may be effectuated within a control tick. The methods described herein may be performed automatically (e.g. by processor(s) associated with the robotic medical system) based on the corresponding desired poses of instruments coupled to the robotic arms and without further user-input.

FIG. 1A shows an example diagram illustrating some components of an example robotic medical system 100 in accordance with certain embodiments disclosed herein. Robotic medical system 100 is merely an illustrative example and the techniques described herein may be applied to various other types of systems. FIGS. 1A-1D are merely illustrative non-limiting examples of systems and mechanisms (e.g. visual interfaces, control interfaces, instrument controllers/manipulators, adaptors, etc.) to facilitate description of example robotic medical system 100. Although some examples are described herein, these examples are not intended to be limiting.

In some embodiments, robotic medical system 100 may comprise a cart or robotic medical device platform 110 (hereinafter "platform 110"), which may be mobile when offline and positioned in proximity to a patient. While platform 110 can be moved (e.g. when offline), typically, platform 110 is stationary and is not moved during a medical procedure (e.g. when online). In some embodiments, platform 110 may comprise staging kinematic chain S 118, which may have one or more degrees of freedom. For example, as shown in FIG. 1A, staging kinematic chain S 118 may be capable of movement vertically along axis 120. However, in some embodiments, staging kinematic chain S 118 may have additional degrees of freedom and may be able to move and/or rotate in other directions. Typically, in conventional systems, a staging arm or staging kinematic chain is not moved (when online) during the medical procedure and is only used (offline) during set up of the system. Once set up, in conventional systems, the staging kinematic chain remains immobile for the duration of the medical procedure.

The term "degrees of freedom" refers to the number of independent parameters that determine the pose of an object. The term "pose" refers to the position (e.g. X, Y, Z coordinates) and orientation (e.g. roll $\phi$, pitch $\theta$, and yaw $\psi$) of an object relative to a frame of reference. Pose (in Cartesian or "task space") may be specified as a 6 Degrees-of-Freedom (DOF) pose, which may include positional coordinates (e.g. X, Y, Z) and orientation information (e.g. roll, pitch, and yaw) relative to a frame of reference (e.g. for the task space). The positional coordinates (X, Y, Z) are also referred to herein as Cartesian coordinates. Orientation can be specified in terms of directional cosines. Various other coordinate systems (e.g. spherical, etc.) may also be used to describe pose. The term "instrument pose" or "end effector pose" may refer to the position and orientation of an instrument and/or end effector relative to a frame of reference. In some instances, instruments may be coupled to end effectors 116. Thus, a change in end effector pose may be reflected in corresponding changes to instrument pose. In some embodiments, the frame of reference may be centered on platform 110. The term "camera pose" or "image sensor pose" may refer to the position and orientation of the image sensor relative to a frame of reference. In some embodiments, the frame of reference may be image sensor centric and may be used to determine the position of one or more instruments (not shown in FIG. 1A) and/or other components relative to the (image sensor centric) frame of reference.

As shown in FIG. 1A, a distal section of staging kinematic chain S 118 is coupled to the corresponding proximal end 114-$r$ of each of the plurality of independently articulable robotic arms A={$A_r$|2≤r≤N, N≥2}, where $A_r$ 112-$r$ represents the $r^{th}$ robotic arm and N represents the number of robotic arms. A proximal section of the staging kinematic chain S 118 may be coupled to the body of platform 110 in a manner that facilitates motion of staging kinematic chain S 118 with one or more degrees of freedom.

The term "independently articulable" in relation to a robotic arm $A_r$ 112-$r$ indicates that the robotic arm $A_r$ 112-$r$ may be moved (i) independently of any other robotic arm $A_u$ 112-$u$, u≠r, where $A_r$, $A_u\varepsilon$A so that movement of robotic arm $A_r$ 112-$r$ may occur without a change to the configuration and/or position of any other robotic arm $A_u$ 112-$u$; and (ii) independently of staging kinematic chain S 118. Further, as shown in FIG. 1A, a robotic arm $A_r$ 112-$r$ may comprise arm sections between joints 113. Joints 113 (e.g. 113-1 . . . 113-N) may include actuators that may move and orient the arm sections to realize a corresponding desired pose $P_r$ for instrument $E_r$ coupled to the robotic arm $A_r$. Each robotic arm $A_r$ 112-$r$ may be coupled to a single distinct corresponding instrument $E_r$ and each instrument $E_r$ may be associated with a corresponding desired pose $P_r$. Instrument $E_r$ (not shown in FIG. 1A) may be coupled to a distal end of 116-$r$ (116-1 . . . 116-N) of a corresponding robotic arm $A_r$ 112-$r$. In some embodiments, distal end of 116-$r$ of robotic arm $A_r$ 112-$r$ may include an instrument control/manipulator, which may be used to manipulate and control instruments $E_r$ coupled to distal end 116-$r$ of robotic arm $A_r$ 112-$r$. For example, an endoscope with instrument $E_r$ may be coupled to distal end 116-$r$ of robotic arm $A_r$ 112-$r$ using the integrated instrument control/manipulator and a desired pose $P_r$ of an instrument $E_r$ may be attained using electromechanical articulation (e.g. through commands/control input from a physician operator).

In general, a configuration of actuators and/or joints to effect a desired pose $P_r$ for an instrument $E_r$ coupled to arm $A_r$ 112-$r$ may be denoted as $C_w=\{C_{w\_r}|1\leq r\leq N\}$, where $C_{w\_r}$ (in joint space) represents a configuration of robot arm $A_r$ 112-$r$. When the staging kinematic chain S 118 is static, a configuration of actuators and/or arm sections to effect a desired pose $P_r$ for an instrument $E_r$ coupled to arm $A_r$ 112-$r$ may be given by $C_{w\_r}$. Because the same desired pose $P_{k\_r}$ for an instrument $E_{k\_r}$ coupled to an arm $A_r$ may be effected with different arm configurations, each distinct configuration of the robotic arms that effects the same desired instrument pose $P_{k\_r}$ is denoted by the subscript "w" in $C_w$. When the staging kinematic chain is moved, the pose $P_r$ for an instrument $E_r$ coupled to arm $A_r$ 112-$r$ may be determined by both $C_{w\_r}$ and $C_S$, where $C_S$ represents a configuration of the staging kinematic chain S 118 (which may correspond to a pose Ps of the staging kinematic chain S 118).

Example platform 110 may include electronic, electromagnetic, and/or electro-mechanical systems to power, control, and operate staging kinematic chain S 118 and the plurality of robot arms A 112. In some embodiments, robotic medical system 100 may also include console 125, which may be coupled to platform 110. For example, console 125 may be electrically and communicatively coupled (e.g. wired or wirelessly) to platform 110.

Example console 125 may include visual interface 135, which may display images including stereoscopic images from image sensors/cameras coupled to one or more robotic arms $A_r$ 112-$r$. Visual interface 135 is merely an illustrative non-limiting example and various other visual interfaces may be used. Example visual interface 135 may also display configuration information for robotic medical system 100 and other relevant information (including graphical information) related to the medical procedure being performed.

In some embodiments, visual interface 135 may take the form of a headset, which may be wirelessly coupled to console 125 and be capable of displaying stereoscopic images and other information. Visual interface 135 may provide a real time indication of instrument pose (position and orientation). In some embodiments, currently selected components (e.g. robot arms 112) and/or the current function selected or being performed using user interface 140 may be displayed or indicated to the user (e.g. as an overlay) in visual interface 135.

In some embodiments, visual interface 135 may include a touchscreen that may accept user input. For example, visual interface 135 may facilitate viewing and interaction with a prior computer tomography (CT) scan and allow a physician/operator to plan a pathway through a patient's body. In some embodiments, visual interface 135 may also facilitate viewing of prior CT scan(s), segmentation of pathways to facilitate visualization and path planning, target selection and identification. In some embodiments, path planning may be based on prior CT scan and/or may be manually modified or generated. In some embodiments, visual interface 135 may also provide set up and/or other instructions (including voice instructions), facilitate menu selection and input, system configuration information, etc.

In some embodiments, robotic medical system 100 may include example user interface 140, which may be used by an operator to select, activate, and control instruments $E_r$ coupled to robotic arms $A_r$. 112-$r$. User interface 140 is merely an illustrative non-limiting example and various other user interfaces may be used. Further, in some embodiments, instruments $E_r$, coupled to robotic arms $A_r$. 112-$r$ may also be autonomously driven (e.g. by a processor or control system based on computer program code). User interface 140 may be communicatively coupled to platform 110 and/or console 125. In some embodiments, user interface 140 may include haptic feedback to alert an operator in relation to various conditions related robotic medical system 100. For example, haptic feedback (e.g. based on the position of instruments 105 relative to the current FOV of image sensors 110) may be received by the user via a haptic interface on user interface 140.

User interface 140 may also include controls such as joysticks, knobs, buttons, etc. which may be used to select a robotic arm $A_r$. 112-$r$ and/or an instrument $E_r$, or to control the pose $P_r$ of the selected robotic arm $A_r$. 112-$r$ and/or instrument $E_r$. Operator selections and movement of instruments may be displayed using visual interface 135. In some embodiments, a real time indication of instrument pose (position and orientation) may be overlaid over images captured by camera(s) coupled to the instrument $E_{k\_r}$. User interface 140 may also facilitate manipulation of and utilization of functionality associated with a selected instrument $E_r$, such as irrigation, aspiration, performing biopsies, taking snapshots, activating pre-programmed sequences, etc. For example, pre-programmed sequences may be based on a pre-operative computed tomography (CT) scan, which may be integrated into an intra-operative interface. In some embodiments, instrument pose may be determined based, on sensory information (e.g. electromagnetic and other sensors) and on information from a prior CT scan.

Figure 1B:
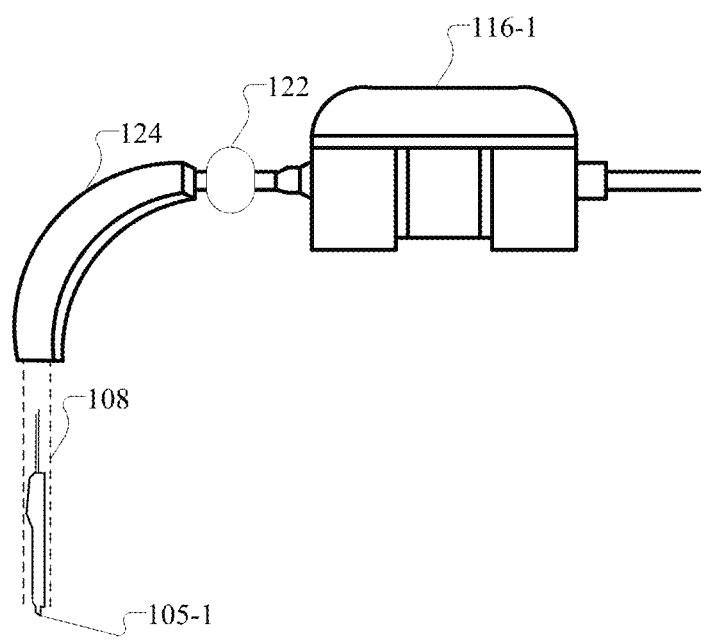
FIG. 1B shows an example instrument coupled to a distal end of a robotic arm.

FIG. 1B shows an example instrument 105-1 coupled to a distal end 116-1 of a robotic arm 112-1 (not shown in FIG. 1B). As outlined above, the example mechanisms (e.g. interfaces, instrument controllers/manipulators, adaptors, catheters, instruments, etc.) described herein are merely illustrative and no limitation is intended. The mechanisms used may depend on the type procedure being performed, and/or other parameters. Thus, the use of other mechanisms (e.g. with various properties—rigid, articulable, flexible, etc., and/or forms, and/or capabilities) that may differ in one or more aspects from the illustrative examples is envisaged in conjunction with techniques described herein, As shown in FIG. 1B distal end 116-1 of a robotic arm 112-1 (not shown in FIG. 1B, #may include an instrument control/manipulator, which may be used to manipulate and control instruments (such as instrument 105-1) coupled to distal end 116-1 using endoscope 108 (shown with dashed lines in FIG. 1B). In FIG. 1B, instrument $E_{1\_1}$ 105-1 is shown as a needle 105-1. In general, various other instruments may be coupled to distal end 116-1 and/or instrument control/manipulator of robotic arm 112-1. Endoscope 108 may include a hollow main sheath through which one or more instruments may be inserted into a patient's body. Endoscope 108 may include an image sensor (e.g. a stereo camera) and other sensors, which may be used to navigate sections of endoscope 108 and instrument (needle) $E_{1\_1}$ 105-1 through a patient's body. For example, images captured by the image sensor may be displayed on visual interface 135 and used during navigation. As shown in FIG. 1B, in some embodiments, robotic medical system may include an adapter 124 and/or other components that may facilitate introduction of endoscope 108 and/or instruments (needle) $E_{1\_1}$ 105-1 into the patient's body. The adaptors and/or other components may depend on the medical procedures being performed and/or on the instruments being used. To place instruments (e.g. needle) $E_1$ 105-1 into a desired pose $P_1$, actuators (not shown in FIG. 1B) in robotic arm $A_1$ 112-1 and/or staging kinematic chain S 118 may be configured in a configuration $C_{w\_1}$ and $C_S$, respectively, to move and orient arm sections of robot arm $A_1$ 112-1 to effect the desired pose $P_1$.

In some embodiments, robotic medical system 100 may also include electro-magnetic field generator/sensor 122, which may generate an electromagnetic field and sense changes to the electromagnetic field to help determine the position of instruments 105-1. In some embodiments, additional sensors coupled to the endoscope 108 and/or instruments 108 may be used, at least in part, to track endoscope 108 and/or determine a pose of instruments 105.

Figure 1C:
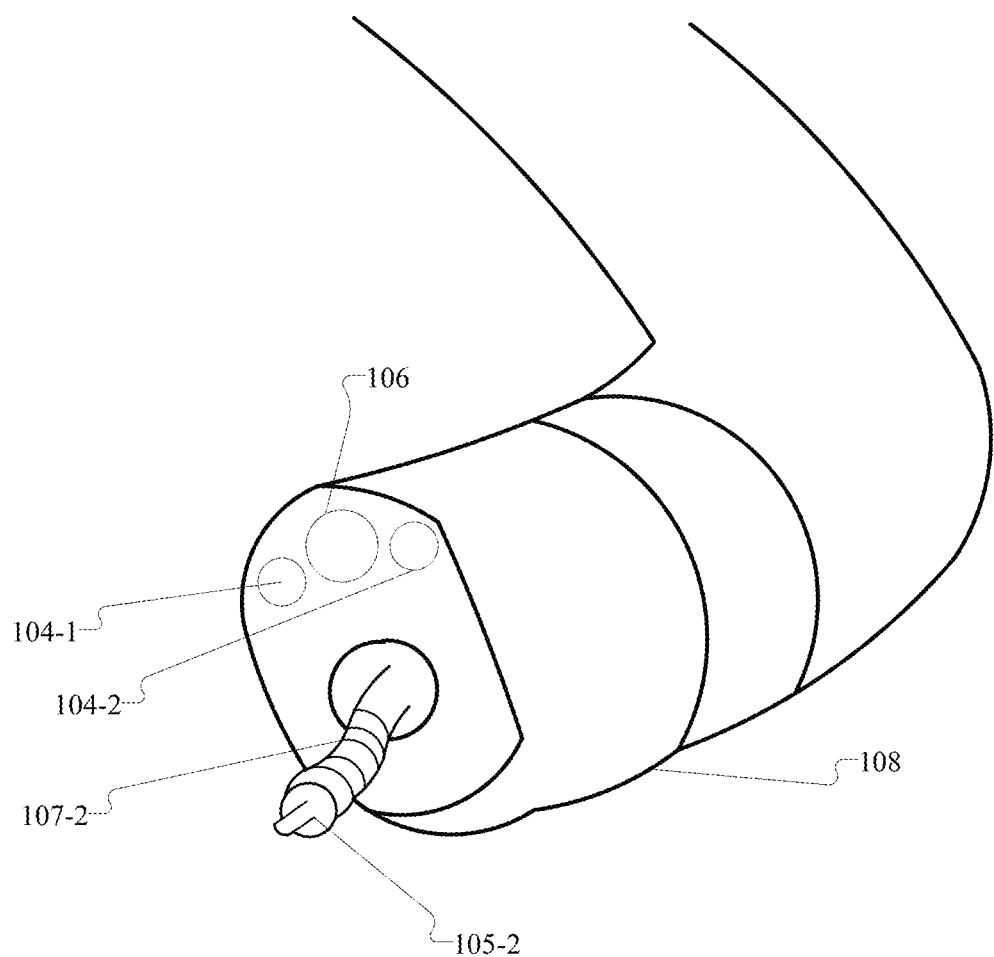
FIG. 1C shows an example endoscope, which may be coupled to a robotic arm, and used to introduce an instrument into a patient's body.

FIG. 1C shows a section of an example endoscope 108, which in some instances, may comprise a flexible hollow main sheath that includes a working channel, which may be used to introduce instruments such as instrument 105-2 (e.g. a cauterizing knife) into a patient's body. In some embodiments, instruments 105 may be coupled to a flexible articulable instrument arm 107 such as instrument arm 107-2, which may be moved and/or oriented based on user input. Instrument arms 107 may be retracted in to the working channel when not in use, or during navigation of the endoscope, and may be activated and extended in accordance during use in accordance with user input. In some embodiments, the working channel (e.g. housing instrument 105 and/or separate working channels within the main sheath of endoscope 108) may also include separate tubing lines (not shown in FIG. 1C) for irrigation, aspiration, etc. FIG. 1C is merely a non-limitation illustrative example. For example, instruments 105 may also be coupled other types of arms (e.g. rigid) depending on the procedure being performed.

In some embodiments, endoscope may also include image sensors 104 (which may be stereoscopic) and light sources 106 for illumination of the surrounding environment. Image sensors 104 may include cameras, CCD sensors, or CMOS sensors, which may transform an optical image into an electronic or digital image and may send captured images to a processor. In some embodiments, image sensors 104 may capture color images, which provide "color information," while "depth information" may be provided by a depth sensor. The term "color information" as used herein refers to color and/or grayscale information. In general, as used herein, a color image or color information may be viewed as comprising 1 to G channels, where G is some integer dependent on the color space being used to store the image. For example, an RGB image may be viewed as comprising three channels, with one channel each for Red, Blue, and Green information. In some embodiments, depth information may be captured using depth sensors (active or passive). The term "depth sensor" is used to refer to functional units that may be used to obtain depth information independently and/or in conjunction with image sensors 110.

In some embodiments, image sensors 104 may form a (passive) stereoscopic image sensor, and may capture stereoscopic images, which may be used to determine depth information. Accordingly, in some embodiments, captured images may include stereoscopic or 3D images with depth information. For example, pixel coordinates of points common to both image sensors (e.g. 104-1 and 104-2) in a captured image may be used along with triangulation techniques to obtain per-pixel depth information. In some embodiments, the depth information may be used, at least in part, to determine the pose of instruments 108 (e.g. relative to image sensors 104 and/or another frame of reference). In some embodiments, visual pose determination techniques may be used in conjunction with information obtained from electromagnetic sensors (e.g. coupled to instruments 105) to determine a current pose of instrument 105. Although, image sensors 104 and light source 106 are shown mounted to the body of endoscope 108, various other configurations are possible. For example, in some embodiments, cameras 104 and light source 106 may also be mounted on individual flexible articulable extensible arms.

Figure 1D:
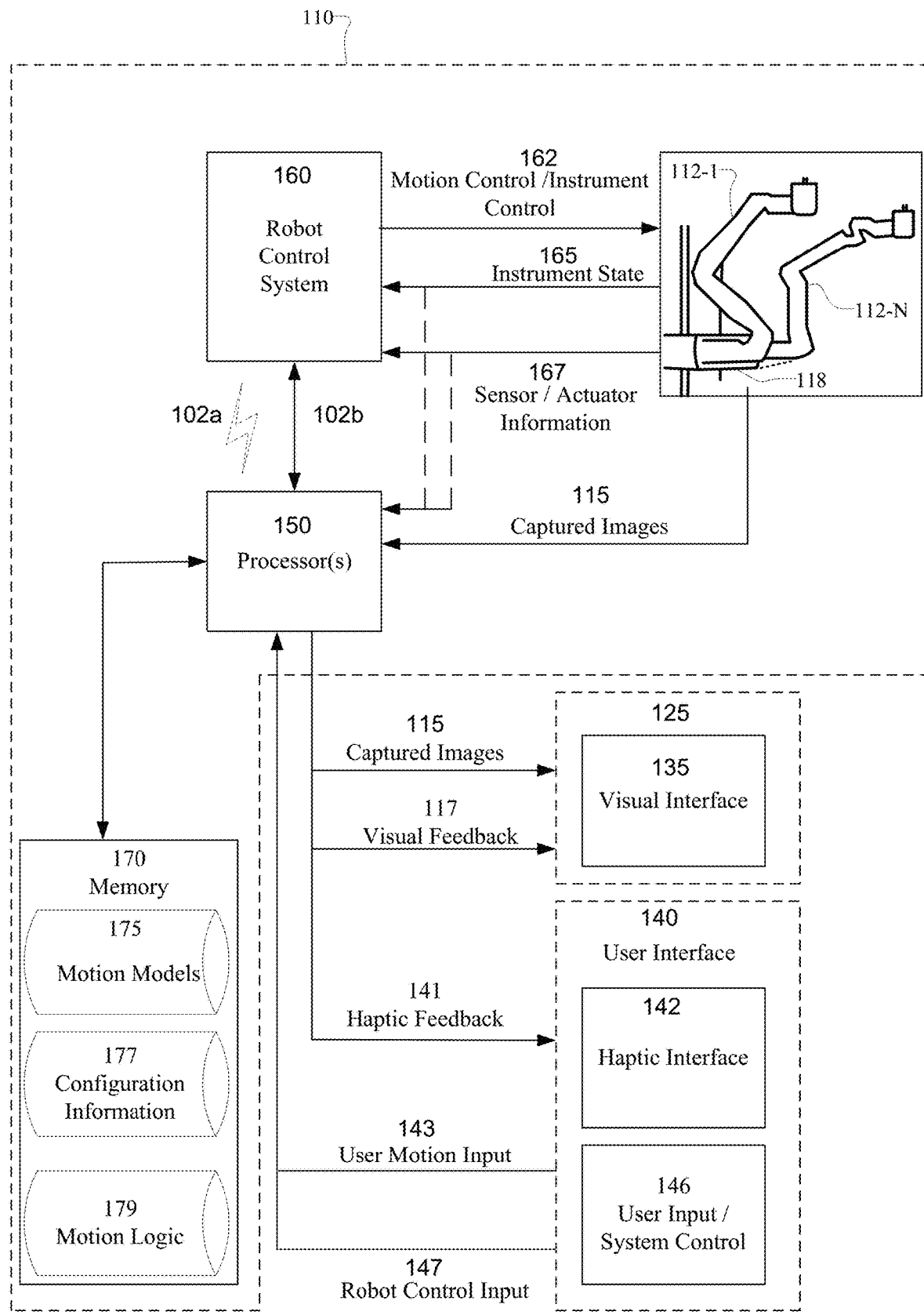
FIG. 1D shows a schematic block diagram illustrating some functional blocks of an example robotic medical system in accordance with certain embodiments disclosed herein.

FIG. 1D shows a schematic block diagram illustrating some functional blocks of an example robotic medical system 100 in accordance with certain embodiments disclosed herein. The functional blocks shown in FIG. 1D and their distribution between platform 110, console 125, and user interface 140 are merely examples and various other configurations of the functional blocks may be used.

As shown in FIG. 1D, robotic medical system 100 may comprise console 125, which may be coupled to visual interface 135 (e.g. a 3D display or stereoscopic display); user interface 140, which may be coupled to haptic interface 142, and user input/system controls 146 (hereinafter referred to as "system controls 146"). The above blocks (console 125, visual interface 135; user interface 140, haptic interface 142, and system controls 146) have been described above in relation to FIGS. 1A-C).

Robotic medical system 100 may further include processor(s) 150, memory 170, and robot control system 160. FIG. 1D is merely exemplary and the functionality associated with blocks shown in FIG. 1B may be combined (e.g. into a single block), or the functionality in a block may be distributed across several blocks. For example, the functionality associated with robot control system block 160 may be integrated within processor(s) 150 block or vice versa. As another example, the functionality associated with processor(s) 150 block may be combined with user interface block 130 or vice versa. As a another example, the functionality associated with processor(s) 150 block, user interface block 130, and robot control system block 160 may be combined. As a further example, the functionality associated with processor(s) 150 block may be distributed between robotic medical device control system block 160 and user interface block 130. For example, each block may have local processor(s) 150 that cooperate (e.g. via commands, signals, and exchange of messages) to enable the functionality described herein. Further, functionality associated with one or more of the functional blocks described may be combined (e.g. in platform 110, console 125, or user interface 140) or distributed (e.g. between platform 110, console 125, and/or user interface 140) as appropriate.

Haptic Interface 142 may provide haptic feedback to signal conditions associated with instruments 105 and/or robotic arms 112, which may be based on user motion input 143. For example, haptic feedback 141 may be based on the position of instruments 105 relative to tissue boundaries and/or the current FOV of image sensors 104 and/or a direction of motion of the instruments 105. Haptic feedback 141 may be received by the user via haptic interface 142. User motion (e.g. via a joystick on user interface 140) may be received by processor(s) 150 as user motion input 143 and communicated to robotic control system 160, which may process the received input and provide appropriate signals to articulate/move the selected and/or active component (one or more of staging kinematic chain S 118, robot arms 112, image sensors 104, and/or instruments 105).

In some embodiments, a user may control and move end effectors and/or instruments 105, while robotic arms 112 and/or staging kinematic chain 118 may be moved automatically (e.g. based on input from processor (s) 150 and/or robot control system 160) to attain the user desired end effector/instrument pose. User Input/System controls block 146 may also provide robot control input 147 to processor(s) 150, which may be processed and communicated to robot control system 160. Robot control system 160 may process the received robot control input 147 and provide appropriate signals to select, activate, deploy, retract, disable, move and/or orient one or more of: (i) robotic arms 112, and/or (ii) actuators coupled to robotic arms 112 and/or staging kinematic chain S 108, and/or arm joints and/or instruments 105, and/or (iii) instruments 105; and/or (iv) other components (e.g. one or more of image sensors 110, light sources, etc.).

In some embodiments, images captured by image sensors 104 (e.g. coupled to corresponding instruments 105) may be processed and displayed on visual interface 135. User motion input 143 (e.g. to move instruments 105) and robot control input 147 (e.g. to control operation of instruments 105) may occur in response to the images displayed on visual interface 135.

In some embodiments, processor(s) 150 may be coupled to memory 170. As shown in FIG. 1B, memory 170 may include motion models block 175, which may be used by processor(s) 150 to control actuators coupled to one or more of: robotic arms 112 and/or staging kinematic chain S 108, and/or arm joints and/or instruments 105 to effect a desired pose. Actuator configuration may facilitate control of: motion and pose of the staging kinematic chain S 108, the motion and pose of robot arms 112-r, and the motion and/or pose of instruments 105. Motion models block 175 may include forward kinematic models, inverse kinematic models and/or calibrated instrument control models.

In some embodiments, motion models block 175 may include both forward and inverse kinematic models pertaining to robotic medical system 100. In some embodiments, motion models block 175 may include a first inverse kinematic model. The first inverse kinematic model may include the robotic arms A 112 and may assume that the staging kinematic chain S 118 is static when determining at a time t1, a first corresponding configuration $C_1=\{C_{1\_r}|1\leq r\leq N\}$ of the robotic arms A 112 that effectuates corresponding desired poses P of instruments E coupled to the robotic arms A 112.

In some embodiments, the first inverse kinematic model may be used to determine a first corresponding configuration $C_1$ of the robotic arms A 112 by determining, for each robotic arm $A_r$ 112-r, corresponding actuator positions. For example, the configuration of arm $A_r$ 112-r may be determined by determining actuator states at various joints associated with robotic arm $A_r$ 112-r. In some embodiments, the corresponding joint positions (or actuator states) $C_{1\_r}=\{c_{1r\_r}|1\leq f\leq F_r\}$ for each robotic arm $A_r$ in joint space may be determined independently of other robotic arms $A_u$, $u\neq r$ and independently of the staging kinematic chain (S). In some embodiments, the first inverse kinematic model may be based on N independent kinematic chains, wherein each kinematic chain corresponds to a robotic arm $A_r$ in the plurality of robotic arms A.

In some embodiments, motion models block 175 may further include a second inverse kinematic model. The second inverse kinematic model may include the robotic arms 112 and may assume mobility of the staging kinematic chain (S), when determining at a time t1, a second corresponding configuration a second corresponding configuration of the robotic arms $C_2=\{C_{2\_r}|1\leq r\leq N\}$ and a configuration Cs to effectuate the corresponding desired poses $P_{k\_Ar}$ of instruments $E_{k\_r}$ coupled to the robotic arms, where Cs is the configuration staging kinematic chain S 118 (which may correspond to a pose Ps of the staging kinematic chain S).

In some embodiments, the second inverse kinematic model may be used to determine the second corresponding configuration $C_2$ of the robotic arms A 112 based on a single kinematic chain, wherein the single kinematic chain combines available degrees of freedom (DoFs) corresponding to all the sub-arms and available DoFs of the staging kinematic chain into the single kinematic chain.

Memory 170 may also store and determine configuration information 177. Configuration information 177 may include current poses P of instruments (or end effectors) 105, current and/or desired configuration/state information (e.g. for actuators, robot arms 112, staging kinematic chain S 118, instruments 105, etc.), information from sensors coupled to robotic medical system 100 (e.g. sensors coupled to staging kinematic chain S 118, robotic arms 112, instruments 105, instrument arms 106, and/or actuators, etc.), and control parameter values for actuators, robot arms 112, staging kinematic chain S 118, etc. The term control parameters may include one or more of: metrics related to the operation of one or more components of robotic medical system 100; and/or system level parameters for robotic medical system 100; and/or parameter ranges for one or more of: actuators, robot arms, and/or instrument motion, and/or disallowed states (e.g. to avoid robot arm collisions); parameters related to the medical procedure being performed (e.g. whether staging kinematic chain may be moved during the procedure and/or portions of the procedure) etc. The configuration information may be used by motion logic block 169 to control actuators and effectuate desired instrument poses P (e.g. based on user input 146).

Motion logic block 179 may obtain and/or determine a set of control parameter values $V=\{V_r|1\leq r\leq N\}$, associated with each robotic arm $A_r$ 112-r based on a current configuration and/or a desired configuration of the robotic arm 112-r (e.g. in relation to desired instrument poses as determined by motion model 165). For example, the control parameter values may be obtained based on the first corresponding configuration $C_1$, where, for each robotic arm $A_r$ 112-r, the corresponding set of control parameter values may be written as $V_r=\{v_{rq}|1\leq q\leq Q_r\}$. In some embodiments, in response to the value of at least one determined control parameter $v_{rq}$ falling outside a corresponding control parameter range (e.g. $v_{rq}<T1$ or $v_{rq}>T2$, where $T1\leq T2$), motion logic may invoke second inverse kinematic model, which may result in motion/change of pose of staging kinematic chain S 118. Accordingly, motion logic block 169 may determine a pose of the staging kinematic chain ($P_S$) and a second corresponding configuration of the robotic arms $C_2=\{C_{r\_2}|1\leq r\leq N\}$ to effectuate the corresponding desired poses $P_{k\_Ar}$, as outlined above.

In some embodiments, at a first time t1, the switch from the first corresponding configuration of the robotic arms $C_1$ to the second corresponding configuration of the robotic arms $C_2$ may be effectuated dynamically during the medical procedure. In some embodiments, after effectuation (e.g. at time t1) of the desired poses based on the second inverse kinematic model, motion logic 169 may initiate a switch back to the first inverse kinematic model. In some embodiments, the first inverse kinematic model may be a default option, and the second inverse kinematic model may be invoked whenever the value of at least one determined control parameter $v_{rq}$ falls outside a corresponding control parameter range.

In some embodiments, the dynamic switch between the first inverse kinematic model to the second inverse kinematic model (or vice versa) may occur within a control tick. In some embodiments, configurations C1 (of robotic arms A 112) or C2 (of robotic arms A 112 and staging kinematic chain S 118), which correspond to desired poses P of instruments E coupled to the robotic arms A 112 may be effectuated within a control tick. The methods described herein may be performed automatically (e.g. by processor(s) 150 and/or robot control system 160 associated with the robotic medical system) based on the corresponding desired poses of instruments coupled to the robotic arms and without further user-input.

The term "control tick" refers to some specified duration of time (or processor cycles) within which motion related computations are completed and new setpoints are transmitted to the actuators. Completing actions within the "control tick" may ensure that the system is perceived as being responsive (with a lower latency) to operator input. In some embodiments, performing the switching between the first inverse kinematic model and the second inverse kinematic model (or vice versa) within a control tick may ensure a seamless user experience.

In some embodiments, motion models block 175 may include calibrated instrument control models, which may be used to estimate an instrument position (e.g. relative to image sensors 110) based on one or more of: sensor/actuator information 167, configuration information 177, instrument state 165, and/or user motion input 143. Configuration information 177 may provide information pertaining to the instruments 105 coupled robotic medical system 100, image sensor configuration (e.g. lens focal length and other parameters), user preferences (e.g. sensitivity to user movement, the desired level of haptic feedback 141, display parameters, disallowed states, etc.) and/or an operational configuration or mode of operation of robotic medical system 100.

In some embodiments, motion models block 175 may also use sensor/actuator information 167 from one or more sensors and actuators in robotic medical system 100. The sensors may include one or more of: electronic sensors; electromagnetic sensors; electro-mechanical sensors, including micro-electro mechanical sensors (MEMS). The sensors may be used to sense actuator articulation/motion of the main sheath, and/or image sensors 110 and/or the image sensor sub-arm, and/or instruments 105 and/or the instrument sub-arms. The sensors may include 3D shape sensing fiber optic sensors; fiber optic force and/or pressure sensors such as photonic crystal fiber (PCF) sensors or Fiber Bragg Grating (FBG) sensors, or make use of scattering arising from FBG sensors, inherently present, or make use of post-process produced Rayleigh scattering. In some embodiments, sensor/Actuator information 167 from one or more sensors may be used in conjunction with captured images to determine instrument pose and/or relative pose.

In some embodiments, the sensors may facilitate instrument pose and/or robot arm and/or staging kinematic chain S 118 configuration determination. Electromagnetic sensors may be embedded in instruments 105 and/or at one or more locations/joints in robotic arms 112 (such as electromagnetic sensor 122), staging kinematic chain S 118, and at other locations. Electromagnetic sensors may use an electromagnetic field generator and small electromagnetic coils to track the instruments. Input from the electromagnetic sensors may be processed (e.g. using signal processing techniques) to determine and track the poses of one or more instruments 105. In some embodiments, signal processing techniques may compensate for distortions in sensor readings that may be caused by the presence of non-magnetic conductive materials in the environment. Electromagnetic tracking and pose determination techniques may operate to determine instrument pose and/or robot arm configuration and/or staging kinematic chain configuration even in situations where there is no line of sight to instruments 105. In some embodiments, input from the electromagnetic sensors may be used by control model 175 to determine a pose (or relative pose) of one or more instruments 105.

Although shown as separate from processor(s) 150, memory 170 may be external and/or internal to processor(s) 150 and may include primary and/or secondary memory. Program code may be stored in memory 170, and read and executed by processor(s) 150 to perform the techniques disclosed herein. As used herein, the term "memory" refers to any type of long term, short term, volatile, nonvolatile, or other memory and is not to be limited to any particular type of memory or number of memories, or type of media upon which memory is stored. Examples of storage media include computer-readable media encoded with databases, data structures, etc. and computer-readable media encoded with computer programs. Computer-readable media may include physical computer storage media. A storage medium may be any available medium that can be accessed by a computer. By way of example, and not limitation, such computer-readable media can comprise Random Access Memory (RAM) and variations thereof including Non-Volatile RAM (NVRAM), Read Only Memory (ROM) and variations thereof Erasable Programmable (EPROM), Flash Memory, etc. Computer-readable media may also include Compact Disc ROM (CD-ROM), memory cards, portable drives, or other optical disk storage, magnetic disk storage, solid state drives, other storage devices, or any other medium that can be used to store desired program code in the form of instructions and/or data structures and that can be accessed by a computer; disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

In some embodiments, processor(s) 150 may process robotic control input 147 and user motion input 143. The processed information may be sent to robot control system 160 (e.g. via wireless communications interface 102a and/or wired communications interface 102b). Robot control system 160 may process the information received from processor(s) 150 and send signals to appropriate actuators on robotic arms 112 and instruments 105 coupled to the robot arms to control, articulate/move, retract, deploy, and/or invoke functionality associated with one or more of: robot arms 112, image sensors 104, and/or instruments 105.

Although shown in FIG. 1D as discrete blocks, processor(s) 150 and/or memory 170 may be distributed between platform 110 (e.g. between robot control system 160) and user console 125 (e.g. which may include visual interface 135), and user interface 140. In one embodiment, platform 110, user interface 140, and console 125 may each have individual local processors 150 and/or local memory. For example, when console 125 is remotely situated from platform 110 and/or user interface 140, console 125 and platform may each have local processors 150. Accordingly, in one embodiment, local processors associated with user interface 140 may be configured to: (a) obtain and transmit user motion input 143 and robot control input 147 to local processors associated with platform 110 (e.g. robot control system 160) and console 125; and (b) receive haptic feedback 141 via haptic interface 142 (e.g. based on input received from robot control system 160 based on one or more of: instrument state 165, sensor/actuator information 167, captured images 115). Further, console 125 may receive and display captured images 115 and provide visual feedback 117 (e.g. to reflect user motion input) using visual interface 135. Conversely, local processors associated with platform 110/robot control system 160 may be configured to: (a) receive user motion input 143 from local processors associated with user interface 140, and (b) robot control input 147 from local processors associated with console 125. Local processors associated with platform 110/robot control system 160 may be configured to provide appropriate motion control/instrument control input 162 to robot arms 112, instruments 105 and other components coupled to platform 110 (e.g. based on the received user motion input 143 and robotic medical device control input 147); and (b) obtain and transmit captured images 115, instrument state 165, and sensor/actuator information 167 (and/or determined image sensor pose, instrument pose information, etc.) to local processors associated with user console 130 and haptic feedback 141 to local processors associated with user interface 140. As another example, memory 170 and some functionality associated with processor(s) 150 may be shared between console 125, platform 110, and user interface 140.

In some embodiments, robot control system 160 may obtain sensor/actuator information 167 from sensors/actuators on robotic medical device 200, captured images 115 from image sensors 110, and instrument state 165. Sensor/actuator information 167, captured images 115, and instrument state 165 may also be received by processor(s) 150 either directly (when coupled to platform 110) or indirectly from robot control system 160 (e.g. over wireless communication interface 102a/wired communications interface 102b). Robot control system 160 may control actuators and/or other electronic, electrical, and electro-mechanical components associated with robot arms 112, staging kinematic chain S 118, and/or instruments 105 based on the received commands (e.g. user motion input 143 and robot control input 147). In some embodiments, robot control system 160 may include functionality to detect and prevent collisions, entanglements, and/or physical contract between robot arms 112 and/or instruments 105. In some embodiments, robot control system 160 may autonomously configure actuators, and/or robot arms 112 and/or staging kinematic chain S 118 based on user motion input 143. For example, in response to user motion input 143 reflecting desired poses P of instruments E 105 coupled to robotic arms A 112, motion models 175, configuration information 177, and motion logic 179 may be used to determine configurations $C_w$ of robot arms A 112, and/or a configuration $C_S$ of staging kinematic chain S 118 (e.g. in joint space) to effectuate the desired poses. In some embodiments, configuration information 177 may include system metrics, actuator parameter ranges, instrument state 165 and/or sensor/actuator information 167 (e.g. actuator values), which may be used to inform determination of the configurations $C_w$ and selection of a final configuration (e.g. $C_1$ or $C_2$).

The methodologies described herein may be implemented in hardware, firmware, software, or any combination thereof. For a hardware implementation, the processor(s) 150 may be implemented within one or more application specific integrated circuits (ASICs), digital signal processors (DSPs), image processors, digital signal processing devices (DSPDs), programmable logic devices (PLDs), field programmable gate arrays (FPGAs), processors, controllers, micro-controllers, microprocessors, electronic devices, other electronic units designed to perform the functions described herein, or any combination thereof. In some embodiments, processor(s) 150 may include capabilities to: process kinematic models, determine poses and/or relative poses of instruments 105, image sensor 104, etc., process images, determine and track corresponding positions of instruments relative to a current image sensor pose, provide input to control haptic feedback 141, provide visual feedback 117, and provide input to control actuators on robot arms 112 and/or staging kinematic chain S 118 and/or instruments 105 to effectuate corresponding desired instrument poses. Processor(s) 150 may also include functionality perform other well-known computer vision and image processing functions such as feature extraction from images, image comparison, image matching, object recognition and tracking, image compression and decompression, etc.

In some embodiments, the communicative coupling between console 125 platform 110 and/or user interface 140 may be wired (e.g. over wired communications interface 102b) or wireless (e.g. over wireless communication interface 102a). For example, commands input by user using console 125 may be wirelessly communicated (e.g. over wireless communication link 102a) to an robot control system 160, which may form part of platform 110. In some embodiments, the robot control system may control and drive robot arms 112, staging kinematic chain S 118, and instruments 105 based on commands received over the communications interface (wired and/or wireless). Wireless communication may include communication over Wireless Local Area Networks (WLAN), which may be based on the IEEE 802.11 standards, and/or over Wireless Wide Area Networks (WWAN), which may be based on cellular communication standards such as a Fifth Generation (5G) network, or Long Term Evolution (LTE). 5G and LTE are described in documents available from an organization known as the 3rd Generation Partnership Project (3GPP).

Thus, in some embodiments, console 125 and user interface 140 may be remotely situated from platform 110, and platform 110 may be controlled and operated based on input received by robot control system 160 over the communications interface. As outlined above, robot control system 160 may control actuators and/or other electronic, electrical, and electro-mechanical components based on the received commands (e.g. from user interface 140/console 125 over communications interface).

In situations where there is an increased danger of risk to medical practitioners or patients (e.g. from infectious/contagious diseases etc.) user interface 140 communicatively coupled (e.g. via wired communications interface 102b and/or wireless communication interface 102a) to robotic medical system 100 may be used at some specified distance or through barriers (e.g. such as optically transparent but biologically protective barriers) to perform medical procedures on the patient while maintaining safety and distancing protocols.

Further, in situations when skilled practitioners are unavailable (e.g. in remote locations), user interface 140 communicatively coupled (e.g. via wired communications interface 102b and/or wireless communication interface 102a) to robotic medical system 100 may be used telesurgically (e.g. via wired communications interface 102b or wireless communication interfaces 102a) to perform or guide performance of medical procedures (e.g. using locally available resources). For example, local medical practitioner(s) may monitor and supervise patient condition and/or the procedure being performed in accordance with any local regulations and/or safety protocols. In the example above, a medical facility deploying robotic medical system 100 may be able to use a remote first medical practitioner (e.g. at a remote first medical facility) for one medical procedure using a first user interface 140-1 (e.g. telesurgically), and use a second medical practitioner (e.g. at a remote second medical facility) for another medical procedure using a second user interface 140-2 telesurgically.

Figure 2A:
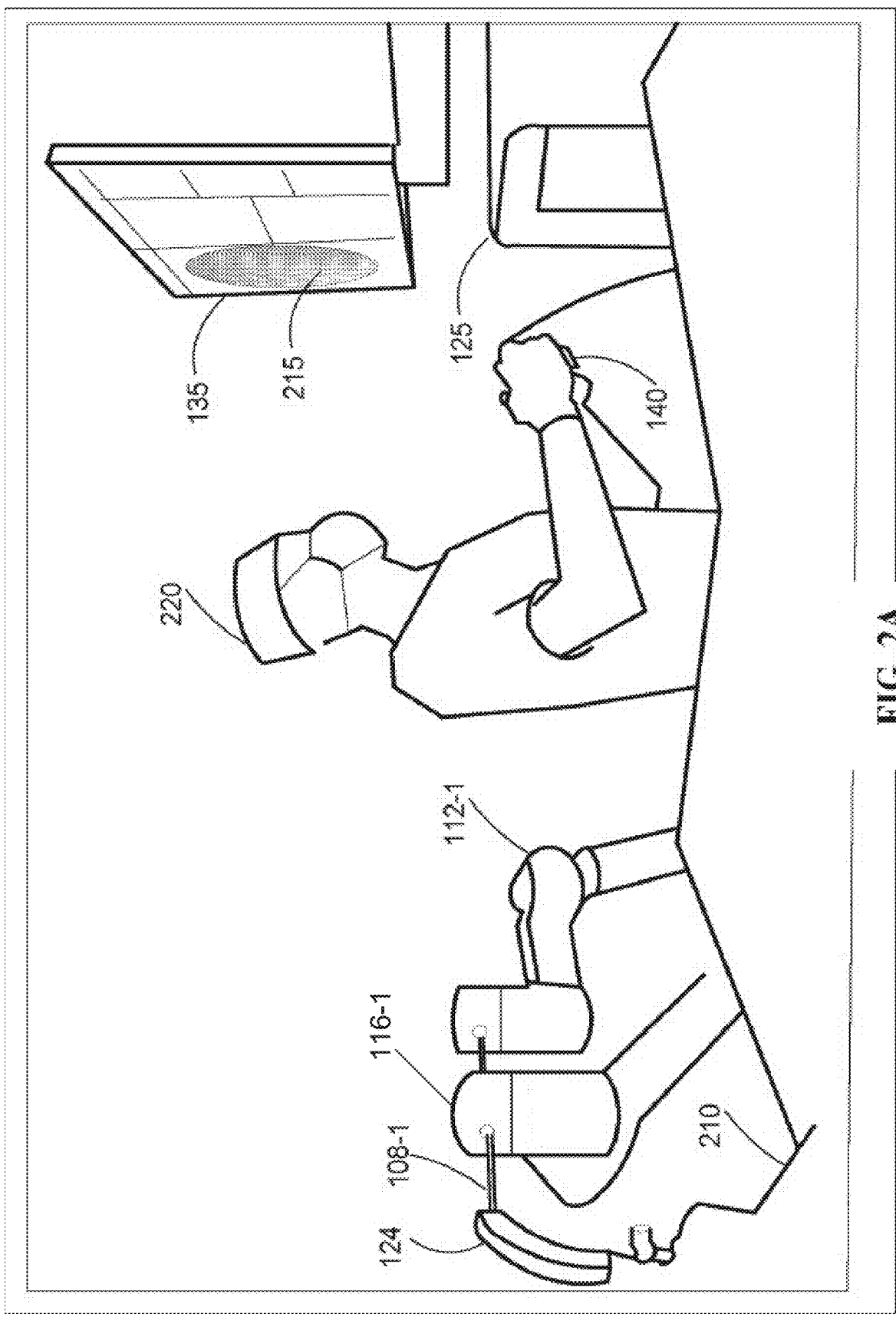
FIGS. 2A and 2B show views illustrating the deployment of robotic arms on example robotic medical system during an example medical procedure.
Figure 2B:
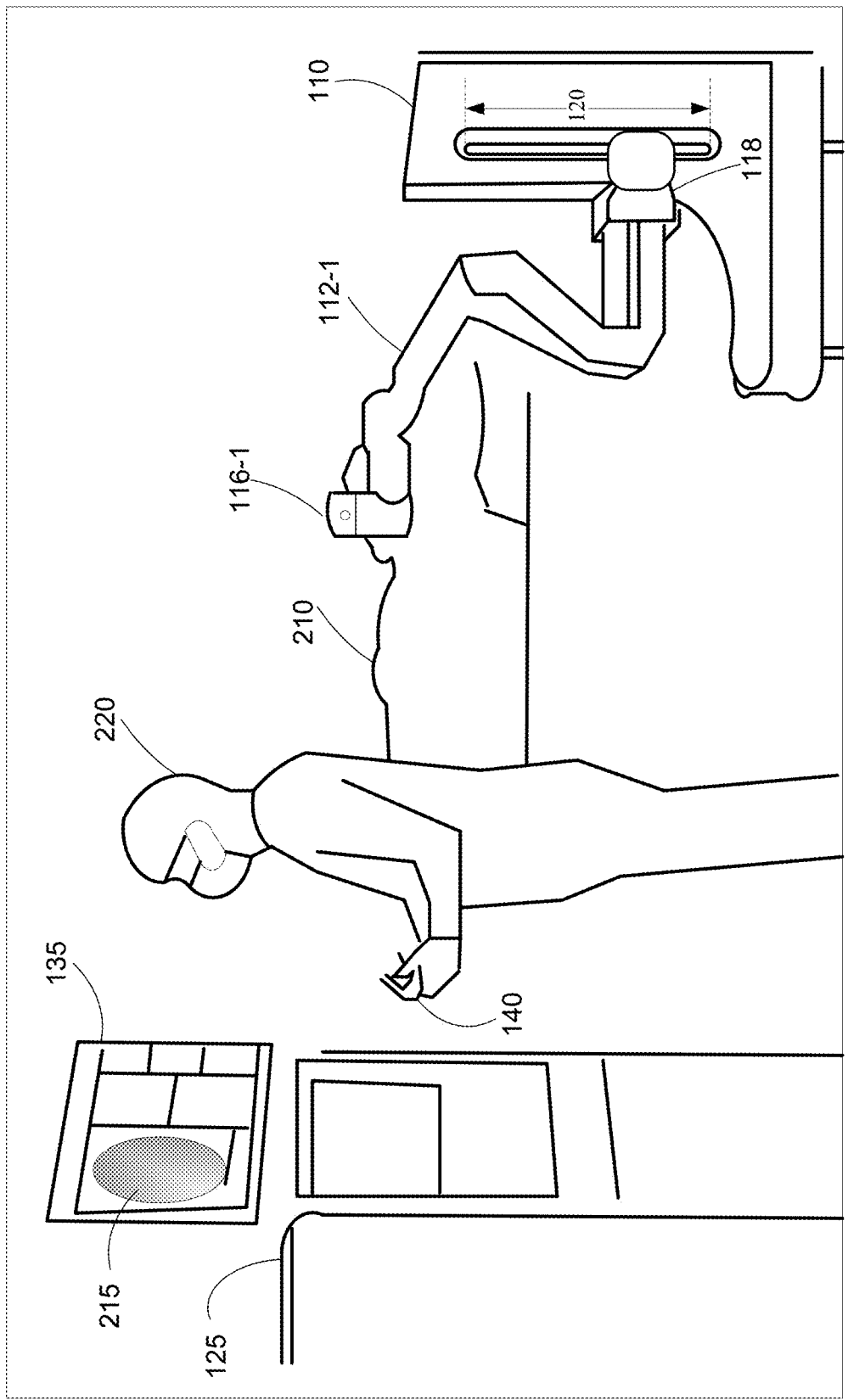

FIGS. 2A and 2B show views illustrating the deployment of robotic arms on example robotic medical system 100 during an example medical procedure. As shown in FIG. 2A, operator (e.g. a physician) 220 may view captured images 215 (e.g. captured by image sensors 104 coupled to an endoscope 108-1) on visual interface 135 coupled to console 125. Based on the displayed image 215, operator 220 may provide user motion input 143 (not shown in FIG. 2A) using user interface 140 to effectuate a desired pose of an instrument 105-1 coupled to endoscope 108-1, which has been coupled distal end of 116-1 of robotic arm $A_1$ 112-1. As shown in FIG. 2A, endoscope 108-1 may be a bronchoscope, which has been inserted through the nasal cavity into patient 210 using adapter 124.

FIG. 2B shows another view illustrating the deployment of robotic arms on example robotic medical system 100 during the example medical procedure of FIG. 2A. As shown in FIG. 2B, operator (e.g. a physician) 220 may view captured images 215 (e.g. captured by image sensors 104 coupled to an endoscope 108-1) on visual interface 135 coupled to console 125. Based on the displayed image 215, operator 220 may provide user motion input 143 (not shown in FIG. 2A) using user interface 140 to effectuate a desired pose of an instrument 105-1 coupled to endoscope 108-1, which has been coupled distal end of 116-1 of robotic arm $A_1$ 112-1 on platform 110. FIG. 2B shows staging kinematic chain S 118 coupled to platform 110. As in FIG. 2B, staging kinematic chain S 118 may be capable of movement along axis 120 during the medical procedure. In general, the number of degrees of freedom available to staging kinematic chain may vary and depend on the type of coupling.

Autonomous control of robot arms 112, staging kinematic chain S 118, and instruments 105 by processor(s) 150 on platform 105 in response to user motion input 143 allows the operator to focus on the medical procedure being performed and removes the cognitive load associated with robot arm and/or staging kinematic chain control. Moreover, in embodiments where platform 110, console 125, and user interface 140 are housed in distinct units that are communicatively coupled, physicians/operators may be able to perform, direct, or guide medical procedures remotely. For example, user commands (via user interface 140) may be relayed over a communications network (e.g. wireless—such as a 5G network) to control instruments poses and functions, and images captured by cameras 104 and other information may be relayed via the communications network to console 125 and displayed via visual interface 135.

Figure 3A:
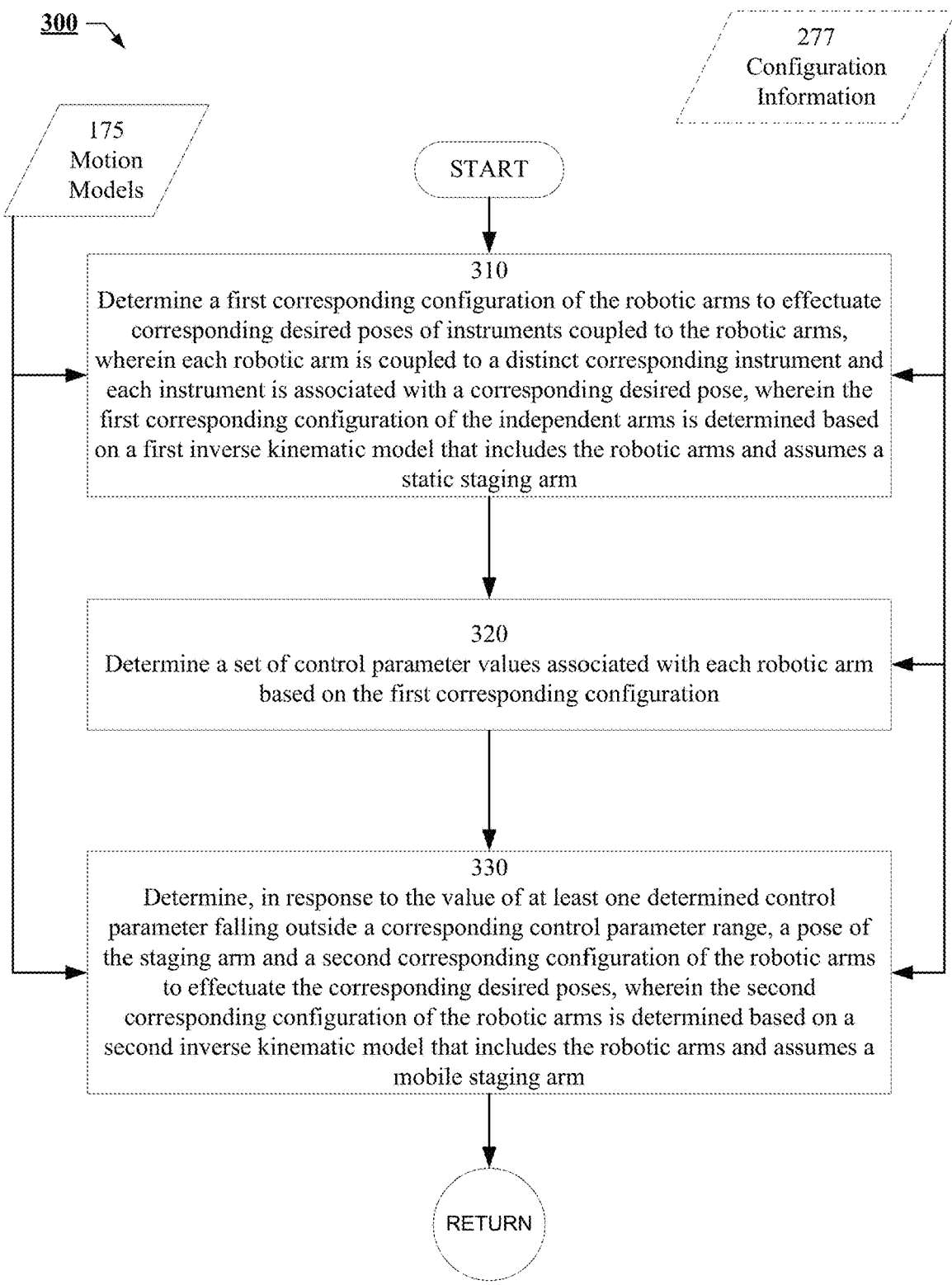
FIG. 3A shows a flowchart of a method to facilitate medical robot motion control during medical procedures in accordance with certain embodiments disclosed herein.

FIG. 3A shows a flowchart of a method 300 to facilitate medical robot motion control during medical procedures. In some embodiments, method 300 may be based on dynamic online kinematic adaptation of arms and/or instruments coupled to a robotic medical system (e.g. robotic medical system 100). In some embodiments, method 300 may be performed by robotic medical system 100 and/or processor(s) 150 and/or robot control system 160 in robotic medical system 100. The term "online" refers to the capability to perform method 300 during a medical procedure. The term "dynamic" refers to the capability to change from one operation mode (e.g. based on a first motion model) to another (e.g. to a second motion model) during the course of effectuating desired poses of one or more instruments coupled to robotic medical system 100. As outlined above, in some embodiments, the operation mode change may occur within a control tick. In some embodiments, the method 300 may be performed automatically in a user-transparent manner based on the corresponding desired poses of instruments coupled to the robotic arms and without further user-input.

In some embodiments, method 300 may be performed on robotic medical system (e.g. robotic medical system 100) comprising a staging kinematic chain (e.g. staging kinematic chain S 118) capable of motion with one or more degrees of freedom (DOF), wherein the staging kinematic chain S 118 is coupled to a plurality of independently articulable robotic arms A={$A_r$|1≤r≤N, N≥2}, where $A_r$ 112 is a robotic arm and N represents the number of robotic arms.

In block 310, (e.g. at a first time) a first configuration of the robotic arms $C_1$={$C_{r\_1}$|1≤r≤N} to effectuate corresponding desired poses of instruments $P_{k\_r}$ coupled to the robotic arms A 112 may be determined based on a first inverse kinematic model that includes the robotic arms and assumes that the staging kinematic chain is static. In some embodiments, each robotic arm $A_r$ 112-r may be coupled to a distinct corresponding instrument $E_r$ 105-r and each instrument $E_r$ 105-r may be associated with a corresponding desired pose $P_r$. As outline above, the first configuration of the independent arms $C_1$ may be determined based on a first inverse kinematic model that includes the robotic arms A 112 and assumes a static staging kinematic chain S 118. For example, in block 310, configuration $C_1$, to effect the desired poses P of instruments E 105 coupled to robot arms A 112, may be determined without movement of staging kinematic chain S 118. In some embodiments, input from motion models 175 and configuration information 177 (e.g. current states of actuators and/or current robotic arm configuration, current staging kinematic chain configuration, current staging kinematic chain pose, etc.) may be used to determine the first corresponding configuration $C_1$.

In some embodiments, (e.g. at time t1) the first inverse kinematic model may determine the first corresponding configuration $C_1$ of the robotic arms A 112 by determining, for each robotic arm $A_r$ 112-r, corresponding robotic arm/joint configurations $C_{1\_r}$={$c_{1r\_f}$|1≤f≤$F_r$}, where $c_{1r\_f}$ represents the first configuration of a joint f associated with robotic arm $A_r$ 112-r and $F_r$ represents the number of joints on robotic arm $A_r$. Each robotic arm $A_r$ 112-r may comprise one or more joints so that 1≤f≤$F_r$. The robotic arm configuration may correspond to actuator states/positions for actuators associated with each joint f on robotic arm $A_r$ 112-r. Accordingly, the corresponding actuator positions for each robotic arm $A_r$ 112-r may be determined independently of any other robotic arm $A_u$ 112-u, u≠r and independently of the staging kinematic chain S 118. Thus, the first inverse kinematic model may be based on (N) independent kinematic chains, wherein a kinematic chain r corresponds to a robotic arm $A_r$ 112-r in the plurality of robotic arms A.

Accordingly, in some embodiments, the first inverse kinematic model may determine the first configuration $C_1$ of the robotic arms by determining, for each of the robotic arms, corresponding actuator positions. For each of the robotic arms, the corresponding actuator positions may be determined independently of the other robotic arms and independently of the staging kinematic chain. Thus, the first inverse kinematic model may be determined based on a plurality of independent kinematic chains, wherein each independent kinematic chain corresponds to a distinct robotic arm and the number of independent kinematic chains may be equal to the total number of the robotic arms.

A Jacobian matrix $J_r$, may be used to describe the linearization of the functional mapping between the position of an instrument (end effector) coupled to a robotic arm $A_r$ 112-r and the corresponding robot arm joint position.

Mathematically, the first inverse kinematic model for robotic arm $A_r$ 112-r may be described based on the Jacobian matrix $J_r$ where $$J_r = \frac{\partial x_r}{\partial C_r}, \tag{1}$$

$$\dot{C}_r^d = (J)^{-1} \dot{x}_r^d \tag{2}$$

where, $x_r$ is the actual (current) Cartesian pose ($X_r$, $Y_r$, $Z_r$) of an instrument coupled to robotic arm $A_r$ 112-r;

$C_r$ is the actual (current) robot arm configuration (joint configuration) of $A_r$ 112-r in joint space, $\dot{C}_r^d$ is the desired joint velocity for $A_r$ 112-r and is determined for each robotic arm $A_r$ 112-r independently, and $\dot{x}_r^d$ is the desired Cartesian instrument velocity for $A_r$ 112-r. Similar equations may be used to determine the orientations associated with each robotic arm $A_r$ 112-r independently.

In block 320, a set of control parameter values associated with each robotic arm based on the first corresponding configuration may be determined.

Each robotic arm $A_r$ in configuration $C_1$ may be associated with a set of control parameter values $V_{r1}$={$v_{r1q}$|1≤q≤$Q_r$, $Q_r$≥1}, so that for robotic medical system 100, the set of control parameter values for the first configuration $C_1$ (e.g. based on the first inverse kinematic model), of the robotic arms A 112 may be written as $V_1 = \{V_{r1} | 1 \leq r \leq N\}$.

In some embodiments, the set of control parameters may comprise one or more of: (a) for each robotic arm, corresponding available degrees of freedom (DoFs); or (b) for each robotic arm, corresponding ranges of motion available to one or more actuators based on a current configuration of the robotic arm; or (c) medical procedure constraints that limit the motion of one or more of the robotic arms; or (d) for each robotic arm, one or more metrics characterizing a corresponding singularity of the robotic arm or corresponding derivatives of the singularity of the robotic arm; or (e) one or more metrics characterizing a singularity of the robotic medical system, or derivatives of the singularity of the robotic medical system including the plurality of robotic arms and the staging kinematic chain; or (f) for each robotic arm, one or more corresponding metrics characterizing the dexterity of the robotic arm, or corresponding derivatives of the dexterity of the robotic arm; or (g) one or more metrics characterizing the dexterity of the robotic medical system, or derivatives of the dexterity of the of the robotic medical system including the plurality of robotic arms and the staging kinematic chain. The control parameters above are merely examples and various other parameters could be used to determine when to switch from the first inverse kinematic model to the second inverse kinematic model.

In some embodiments, the determination of metrics for singularity and/or dexterity may be based on computing the singular values of the Jacobian matrix. For example, a first method may use a conditional number, which may be a ratio $$\left(\frac{\Sigma_{max}}{\Sigma_{min}}\right)$$

of the largest singular value ($\Sigma_{max}$) to the smallest singular value ($\Sigma_{min}$). A second method may use the manipulability $\mu$, which refers to the product of the singular values or equivalents may be computed as $\sqrt{|JJ^T|}$. Derivatives of the metrics may be the partial derivatives of the above metrics such as $$\frac{\partial \mu}{\partial C}.$$

In some embodiments, in block 330, in response to the value of at least one determined control parameter $v_{rq}$ falling outside a corresponding control parameter range ((e.g. $v_{rq} < T1$ or $v_{rq} > T2$), a pose of the staging kinematic chain ($P_S$) and a second corresponding configuration of the robotic arms $C_2 = \{C_{2\_r}, |1 \leq r \leq N\}$ and a configuration $C_S$ of staging kinematic chain S 118 to effectuate the corresponding desired poses $P_{k\_Ar}$ may be determined, wherein the second corresponding configuration of the robotic arms $C_2$ and configuration $C_S$ of staging kinematic chain S 118 is determined based on a second inverse kinematic model that includes the robotic arms and assumes a mobile staging kinematic chain. Configuration Cs may correspond to a pose Ps of the staging kinematic chain S.

Mathematically, the second inverse kinematic model for robotic medical system 100 may be described in terms of the Jacobian matrix $J_C$, where $$J_A = \begin{bmatrix} J_1 & 0 & \cdots & 0 & J_s \\ 0 & J_2 & \cdots & 0 & J_s \\ 0 & 0 & \ddots & 0 & J_s \\ 0 & 0 & \cdots & J_N & J_s \end{bmatrix}, \quad (3)$$

where, $J_r$, $1 \leq r \leq N$, is the Jacobian matrix for robotic arm $A_r$ 112-$r$ $J_S$ is the Jacobian matrix for staging kinematic chain S 118, Further, if $x_A^d$ represents the combined desired Cartesian poses P for all instruments coupled to robotic arms A 112 and $\dot{x}_A^d$ represents the combined desired Cartesian velocities for all instruments coupled to robotic arms A 112, then $$x_A^d = \begin{bmatrix} x_1^d \\ \vdots \\ x_N^d \end{bmatrix}, \dot{x}_A^d = \begin{bmatrix} \dot{x}_1^d \\ \vdots \\ \dot{x}_N^d \end{bmatrix}, \quad (4)$$

$$C_A^d = \begin{bmatrix} c_1^d \\ \vdots \\ c_N^d \\ c_S^d \end{bmatrix}, \text{ and } \dot{C}_A^d = \begin{bmatrix} \dot{c}_1^d \\ \vdots \\ \dot{c}_N^d \\ \dot{c}_S^d \end{bmatrix}, \text{ and } \dot{C}_A^d = (J_A)^{-1} \dot{x}_A^d$$

The equations above may be used, in the second inverse kinematic model, to determine the desired configuration of all arms A 112 and of the staging kinematic chain S 118. Similar equations may be used to determine the orientations associated with all arms A 112 and the orientations of the staging kinematic chain S 118.

Thus, in step 330, in response to at least one determined control parameter value falling outside a corresponding control parameter range, a pose of the staging kinematic chain and a second configuration of the robotic arms to effectuate the one or more corresponding desired poses of the one or more instruments may be determined, wherein the second configuration may be determined based on a second inverse kinematic model that includes the robotic arms and assumes that the staging kinematic chain is mobile.

Accordingly, the second inverse kinematic model determines the second corresponding configuration of the robotic arms based on a single kinematic chain that combines available degrees of freedom (DoFs) corresponding to all the sub-arms and available DoFs of the staging kinematic chain.

Figure 3B:
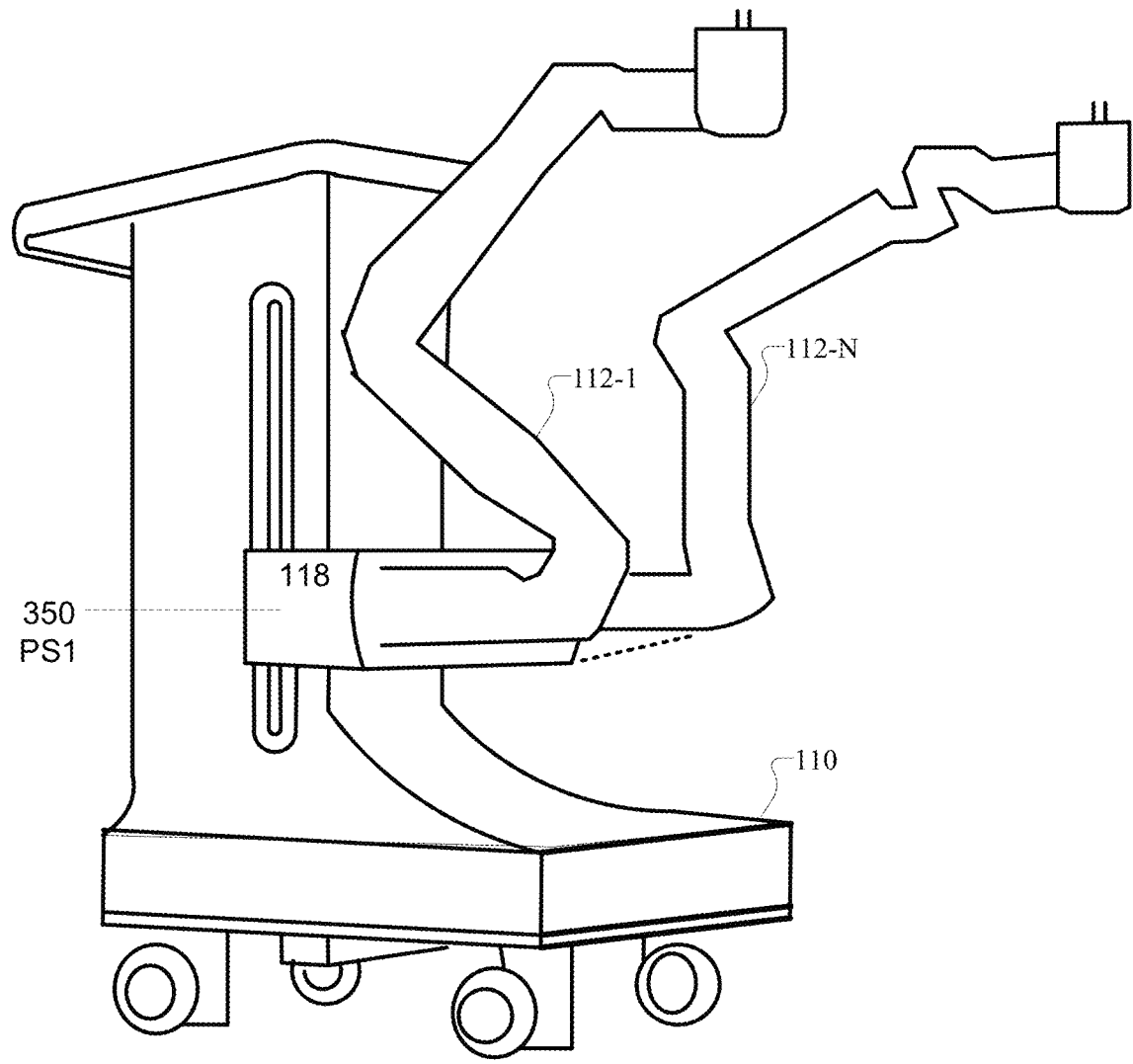
FIGS. 3B and 3C show platform 110 with staging kinematic chain S 118 being moved from an initial position (in FIG. 3B) to a subsequent position (in FIG. 3C) during a medical procedure in accordance with certain embodiments disclosed herein.
Figure 3C:
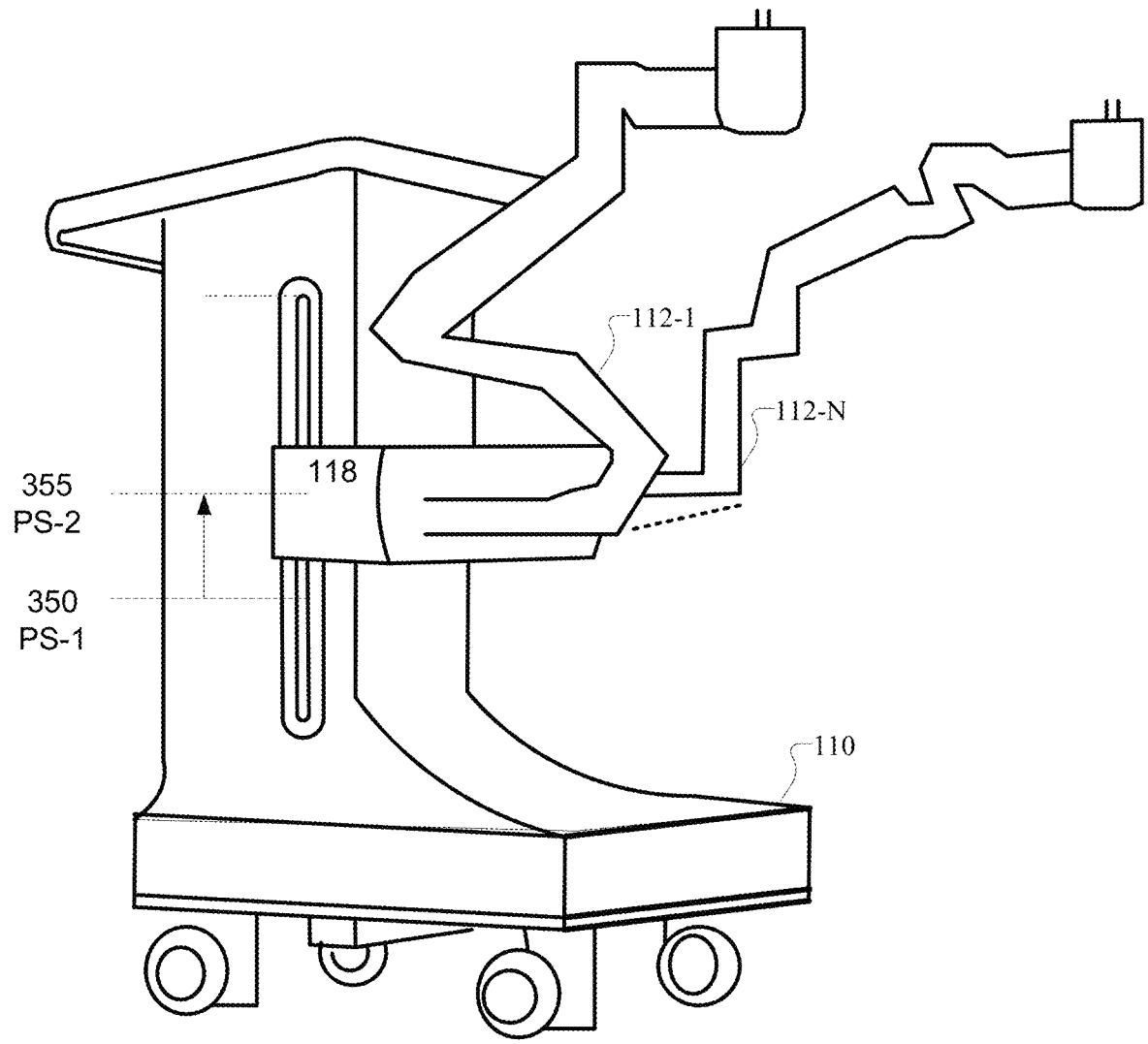

FIGS. 3B and 3C shows platform 110 with staging kinematic chain S 118 being moved from an initial position (in FIG. 3B) to a subsequent position (in FIG. 3C) dynamically during a medical procedure in accordance with certain embodiments disclosed herein.

FIG. 3B shows platform 110 with staging kinematic chain S 118 in position PS-1 350. FIG. 3C shows platform 110 with staging kinematic chain S 118 in subsequent position PS-2 355. As shown in FIG. 3C, in response to a determination that one or more control parameters may fall outside a pre-determined range when robotic arms A 112 are configured as per the first configuration, a second configuration may be determined and, staging kinematic chain S 118 may be moved to position PS-2 355 (from prior position PS-1 350) in accordance with the second configuration to effect the desired poses of instruments coupled to robotic arms A 112. The movement of staging kinematic chain S 118 may be moved and repositioned when: (a) robotic medical system is online and (b) dynamically, in response to a determination that one or more control parameters may fall outside a pre-determined range when robotic arms A 112 are configured as per the first configuration. For example, the switch from the first corresponding configuration of the robotic arms (e.g. as determined in block 310) and the second corresponding configuration of the robotic arms (e.g. as determined in block 330) may be effectuated dynamically during a medical procedure being performed. In some embodiments, in method 300, the corresponding desired poses of instruments coupled to the robotic arms may be effectuated within a control tick.

In some embodiments, method 300 may further comprise (e.g. following step 330) determining, based on policies associated with a medical procedure being performed, whether the corresponding desired poses of the instruments coupled to the robotic arms can be effectuated based on the pose of the staging kinematic chain and the second corresponding configuration of the robotic arms; and in response to a determination that the pose of the staging kinematic chain and the second corresponding configuration of the robotic arms would result in at least one policy violation, effectuating the corresponding desired poses of the instruments in accordance with the first corresponding configuration of the robotic arms without movement of the staging kinematic chain.

In some embodiments, method 300 may further comprise dynamically switching, upon effectuation of the corresponding desired poses of instruments coupled to the robotic arms, to the first inverse kinematic model. For example, the first inverse kinematic model may be a default option, and the second inverse kinematic model may be invoked whenever the value of at least one determined control parameter $v_{rq}$ falls outside a corresponding control parameter range.

Thus, in some embodiments, method 300 may dynamically revert or switch back to the first inverse kinematic model after effectuating the corresponding desired poses of the instruments based on the second inverse kinematic model. In some embodiments, the method may be performed automatically during a medical procedure based on the one or more corresponding desired poses of the one or more instruments and without further user-input. For example, the switching between the first inverse kinematic model and the second inverse kinematic model may occur in a manner transparent to the user. User motion input 143 may automatically trigger a switch from the first inverse kinematic model to the second inverse kinematic model (or vice versa) without any additional user input. Thus, the staging kinematic chain 118 may be automatically moved (e.g. based on the second inverse kinematic model) as appropriate based on user motion input thereby facilitating operator focus on the medical procedure and relieving operators of the cognitive load associated with system configuration and motion.

In some embodiments, method 300 may be performed on robotic medical system 100, which may comprise: a staging kinematic chain S 118, capable of motion with one or more degrees of freedom (DOF), a plurality of instruments 105, a plurality of independently articulable robotic arms A 112, wherein a proximal end of each robotic arm 112-*r* is coupled to the staging kinematic chain S 118, wherein a distal end of each robotic arm 112-*r* is coupled to at least one corresponding instrument 105, and a processor 150 operationally coupled to the staging kinematic chain S 118, the plurality of robotic arms A 112, and the plurality of instruments 105, wherein the processor is configured to perform method 300 as outlined above.

Figure 4:
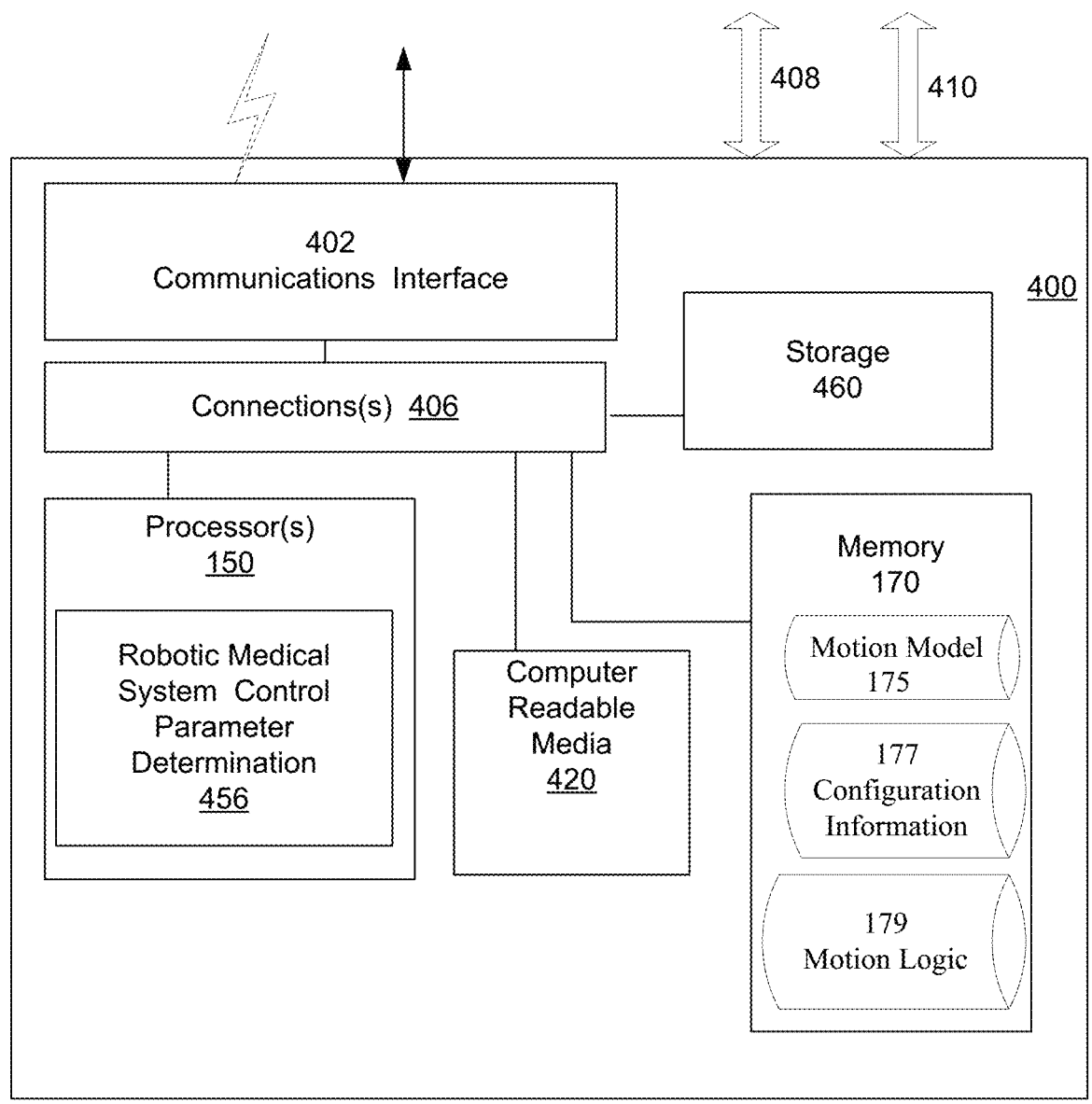
FIG. 4 shows an exemplary computing subsystem to facilitate medical robot motion control during medical procedures.

FIG. 4 shows an exemplary computing subsystem 400 to facilitate medical robot motion control during medical procedures. Computing subsystem 400 may form a part of robotic medical system 100. For example, computing subsystem 400 may form part of platform 110, and/or robot control system 160, and/or console 125 may be operationally coupled to robot arms 112, and/or staging kinematic chain 118, and/or instruments 105 and/or visual interface 134 and/or user interface 140.

As shown in FIG. 4, computing subsystem 400 may include processor(s) 150, memory 170, and communications interface 402, which may be connected using connections 406. Connections 406 may take the form of buses, lines, fibers, electronic interfaces, links, etc., which may operationally couple the above components.

Communications interface 402 may be capable of wired (e.g. using wired communications interface 102*b*) or wireless (e.g. using wireless communication interface 102*a*) communications with another device or component (e.g., user interface 140, and/or console 125). Captured images 115, instrument state 165 (which may include poses of instruments), robot arm configuration information, sensor/actuator information 167, staging kinematic chain pose, etc., may be received over communications interface 402. User input may also be transmitted (e.g. when computing subsystem is part of user interface 140 and/or console 125) or received (e.g. when computing subsystem forms part of robot control system 160) using communications interface 402. Wireless communication may include communication over Wireless Local Area Networks (WLAN), which may be based on the IEEE 802.11 standards, and/or over Wireless Wide Area Networks (WWAN), which may be based on cellular communication standards such as a Fifth Generation (5G) network, or Long Term Evolution (LTE).

Computing subsystem 400 may also include control interface 408, which may provide control input (e.g. to activate, select, deploy, deactivate, move, orient, retract, extend, etc.) and command input (e.g. to exercise functions) that drives robotic arms 112, staging kinematic chains, and/or instruments 105. In some embodiments, control interface 408 may also output haptic feedback 141 (e.g. to indicate instrument state and/or guide user input related to instrument movement direction). Control interface 408 may communicate with processor(s) 150 and may be controlled by processor(s) 150.

Computing subsystem 400 may also include display interface 410, which may interact with display 135 (e.g. a 3D or stereoscopic display) to provide visual feedback 117 (e.g. configuration information, instrument position related information, procedure related information, system state information, etc.). For example, display interface may generate graphics, and/or other visualization, which may augment or overlay the captured images 115. Display interface 410 may communicate with processor(s) 150 and may be controlled by processor(s) 150.

In some embodiments, memory 170 may comprise main or primary memory (e.g. RAM) and storage 460. Program code may be stored in memory 170, and read and executed by processor(s) 150 to perform the techniques disclosed herein. Storage 460 may include ROM, EPROM, NVRAM, flash memory, secondary storage, and other computer readable media (e.g. fixed and/or removable drives, optical disks, etc.). Computer-readable media 420 may be encoded with databases, data structures, etc. and/or with computer programs. By way of example, and not limitation, such computer-readable media may also include CD-ROM, memory cards, portable drives, or other optical disk storage, magnetic disk storage, solid state drives, other storage devices, or any other medium that can be used to store desired program code in the form of instructions and/or data structures and that can be accessed by a computer.

In some embodiments, images captured by image sensors 104, instrument state 165, sensor/actuator information 167, motion control/instrument control input 162, configuration information 177, instrument poses, robotic arm configuration, staging kinematic chain pose, procedural policies that affect robotic operation, control parameter ranges, and other information pertaining to robotic medical system 100 may be stored in memory 170 for operational, training, logging, and other purposes. For example, based on user input and robotic medical system configuration, a procedure performed by robotic medical system 100 may be recorded and replayed/analyzed at a subsequent time. As another example, the procedure may be live streamed via communications interface 402 (e.g. for educational or training purposes).

Memory 170 may motion models 175, which may include kinematic and inverse kinematic models for robotic medical system 100. In some embodiments, motion models 175 may also include calibrated instrument control models, which may be used to estimate an instrument pose based on one or more of: motion control/instrument control input 162, configuration information 177, and/or user motion input 143. In some embodiments, control model 175 may also use information from one or more sensors (when present) in robotic medical system 100. Motion models may also include information to determine robotic arm configuration and staging kinematic chain pose and staging kinematic chain configuration.

Memory 170 may include configuration information 177, which may provide information pertaining to the instruments on robotic medical system 100, image sensor configuration (e.g. lens focal length and other parameters), user preferences (e.g. sensitivity to user movement, the desired level of haptic feedback 141, display parameters, etc.) and/or an operational configuration or mode of operation of robotic medical system 100 (e.g. indicating whether staging kinematic chain S 118 may be moved during a procedure or a portion of the procedure).

The methodologies described herein may be implemented in hardware, firmware, software, or any combination thereof. For a hardware implementation, the processor(s) 150 may be implemented within one or more application specific integrated circuits (ASICs), digital signal processors (DSPs), image processors, digital signal processing devices (DSPDs), programmable logic devices (PLDs), field programmable gate arrays (FPGAs), processors, controllers, micro-controllers, microprocessors, electronic devices, other electronic units designed to perform the functions described herein, or any combination thereof. In some embodiments, processor(s) 150 may include capabilities to: process motion models including kinematic models, determine robot arm configuration, staging kinematic chain configuration, determine actuator input to effect a determined arm configuration, determine robot arm configurations to effect an instrument pose, determine an instrument pose from robot arm configuration, etc. Processor(s) 150 may also include functionality perform other well-known computer vision and image processing functions such as feature extraction from images, image comparison, image matching, object recognition and tracking, image compression and decompression, etc.

Although the present disclosure is described in connection with specific embodiments for instructional purposes, the disclosure is not limited thereto. Various adaptations and modifications may be made to the disclosure without departing from the scope. Therefore, the spirit and scope of the appended claims should not be limited to the foregoing description.

What is claimed is:

1. A method on a robotic medical system comprising a staging kinematic chain capable of motion with one or more degrees of freedom (DOF), wherein the staging kinematic chain is coupled to a plurality of independently articulable robotic arms, the method comprising:
   determining a first configuration of the robotic arms based on a first inverse kinematic model that includes the robotic arms and assumes that the staging kinematic chain is static, wherein:
      the first configuration of the robotic arms effectuates one or more corresponding desired poses of one or more instruments coupled to the robotic arms;
      proximal ends of the robotic arms are coupled to a same mobile portion of the staging kinematic chain; and
      the first inverse kinematic model is based on a plurality of independent kinematic chains, wherein each independent kinematic chain corresponds to a distinct robotic arm;
   determining a set of control parameter values associated with one or more of the robotic arms based on the first configuration; and
   determining, in response to at least one determined control parameter value falling outside a corresponding control parameter range of the parameter values, a pose of the staging kinematic chain and a second configuration of the robotic arms to effectuate the one or more corresponding desired poses of the one or more instruments, wherein the second configuration is determined based on a second inverse kinematic model that includes the robotic arms and assumes that the staging kinematic chain is mobile.

2. The method of claim 1, wherein the first inverse kinematic model determines the first configuration of the robotic arms by determining, for each of the robotic arms, corresponding actuator positions.

3. The method of claim 2, wherein, for each of the robotic arms, the corresponding actuator positions are determined independently of the other robotic arms and independently of the staging kinematic chain.

4. The method of claim 1, wherein a count of the plurality of independent kinematic chains is equal to a total number of the robotic arms.

5. The method of claim 1, further comprising:
   dynamically switching to the first inverse kinematic model upon effectuation of the one or more corresponding desired poses of the one or more instruments based on the second inverse kinematic model.

6. The method of claim 1, wherein the method is performed automatically during a medical procedure based on the one or more corresponding desired poses of the one or more instruments and without further user-input.

7. The method of claim 1, wherein the set of control parameter values associated with one or more of the robotic arms comprise one or more of:
   corresponding degrees of freedom (DoFs) available to the one or more robotic arms; or
   corresponding ranges of motion available to one or more actuators based on a current configuration of the one or more robotic arms; or
   medical procedure constraints that limit motion of the one or more robotic arms; or
   one or more first metrics characterizing a corresponding singularity of at least one robotic arm or corresponding derivatives of the singularity of the at least one robotic arm; or one or more second metrics characterizing dexterity of the at least one robotic arm, or
corresponding derivatives of the dexterity of the at least one robotic arm; or
one or more third metrics characterizing a singularity of the robotic medical system, or derivatives of the singularity of the robotic medical system including the plurality of robotic arms and the staging kinematic chain; or
one or more fourth metrics characterizing the dexterity of the robotic medical system, or derivatives of the dexterity of the of the robotic medical system including the plurality of robotic arms and the staging kinematic chain.

8. The method of claim 1, further comprising:
determining, based on policies associated with a medical procedure being performed, whether the one or more corresponding desired poses of the one or more instruments can be effectuated based on the pose of the staging kinematic chain and the second configuration of the robotic arms; and
in response to a determination that the pose of the staging kinematic chain and the second configuration of the robotic arms would result in at least one violation of the policies, effectuating the corresponding desired poses of the one or more instruments in accordance with the first configuration of the robotic arms without movement of the staging kinematic chain.

9. The method of claim 1, wherein the second inverse kinematic model is used to determine the second configuration of the robotic arms based on a single kinematic chain, wherein the single kinematic chain combines available degrees of freedom (DoFs) corresponding to the plurality of robotic arms and available DoFs of the staging kinematic chain into the single kinematic chain.

10. The method of claim 1, further comprising:
effectuating either the first configuration of the robotic arms or the second configuration of the robotic arms dynamically during a medical procedure.

11. The method of claim 10, wherein the effectuation of either the first configuration of the robotic arms or the second configuration of the robotic arms occurs within a control tick.

12. A robotic medical system comprising:
a staging kinematic chain, capable of motion with one or more degrees of freedom (DOF);
a plurality of independently articulable robotic arms coupled to the staging kinematic chain;
one or more instruments coupled to the robotic arms; and
a processor operationally coupled to the staging kinematic chain, the plurality of robotic arms, and the one or more instruments, wherein the processor is configured to:
determine a first configuration of the robotic arms based on a first inverse kinematic model that includes the robotic arms and assumes that the staging kinematic chain is static, wherein:
the first configuration of the robotic arms effectuates one or more corresponding desired poses of the one or more instruments coupled to the robotic arms;
proximal ends of the robotic arms are coupled to a same mobile portion of the staging kinematic chain; and
the first inverse kinematic model is based on a plurality of independent kinematic chains, wherein each independent kinematic chain corresponds to a distinct robotic arm;
determine a set of control parameter values associated with one or more of the robotic arms based on the first configuration; and
determine, in response to at least one determined control parameter value falling outside a corresponding control parameter range of the parameter values, a pose of the staging kinematic chain and a second configuration of the robotic arms to effectuate the one or more corresponding desired poses of the one or more instruments, wherein the second configuration is determined based on a second inverse kinematic model that includes the robotic arms and assumes that the staging kinematic chain is mobile.

13. The robotic medical system of claim 12, wherein the processor is further configured to:
dynamically switch to the first inverse kinematic model upon effectuation of the one or more corresponding desired poses of the one or more instruments based on the second inverse kinematic model.

14. The robotic medical system of claim 12, wherein the processor is further configured to:
automatically effectuate either the first configuration of the robotic arms or the second configuration of the robotic arms dynamically during a medical procedure.

15. The robotic medical system of claim 14, wherein the effectuation of either the first configuration of the robotic arms or the second configuration of the robotic arms occurs within a control tick.

16. The robotic medical system of claim 12, wherein the set of control parameter values associated with one or more of the robotic arms comprise one or more of:
corresponding degrees of freedom (DoFs) available to the one or more robotic arms; or corresponding ranges of motion available to one or more actuators based on a current configuration of the one or more robotic arms; or
medical procedure constraints that limit motion of the one or more robotic arms; or
one or more first metrics characterizing a corresponding singularity of at least one robotic arm or corresponding derivatives of the singularity of the at least one robotic arm; or
one or more second metrics characterizing dexterity of the at least one robotic arm, or
corresponding derivatives of the dexterity of the at least one robotic arm; or
one or more third metrics characterizing a singularity of the robotic medical system, or derivatives of the singularity of the robotic medical system including the plurality of robotic arms and the staging kinematic chain; or
one or more fourth metrics characterizing the dexterity of the robotic medical system, or derivatives of the dexterity of the of the robotic medical system including the plurality of robotic arms and the staging kinematic chain.

17. The robotic medical system of claim 12, wherein the second inverse kinematic model is used to determine the second configuration of the robotic arms based on a single kinematic chain, wherein the single kinematic chain combines available degrees of freedom (DoFs) corresponding to the plurality of robotic arms and available DoFs of the staging kinematic chain into the single kinematic chain.

18. A non-transitory computer-readable medium comprising instructions to configure a processor coupled to a robotic medical system to:
  determine a first configuration of a plurality of independently articulable robotic arms based on a first inverse kinematic model that includes the robotic arms and assumes that a staging kinematic chain is static, wherein:
    the first configuration of the robotic arms effectuates one or more corresponding desired poses of one or more instruments coupled to the robotic arms;
    proximal ends of the robotic arms are coupled to a same mobile portion of the staging kinematic chain; and
    the first inverse kinematic model is based on a plurality of independent kinematic chains, wherein each independent kinematic chain corresponds to a distinct robotic arm;
  determine a set of control parameter values associated with one or more of the robotic arms based on the first configuration; and
  determine, in response to at least one determined control parameter value falling outside a corresponding control parameter range of the parameter values, a pose of the staging kinematic chain and a second configuration of the robotic arms to effectuate the one or more corresponding desired poses of the one or more instruments, wherein the second configuration is determined based on a second inverse kinematic model that includes the robotic arms and assumes that the staging kinematic chain is mobile.

19. The non-transitory computer-readable medium of claim 18, wherein the second inverse kinematic model is used to determine the second configuration of the robotic arms based on a single kinematic chain, wherein the single kinematic chain combines available degrees of freedom (DoFs) corresponding to the plurality of robotic arms and available DoFs of the staging kinematic chain into the single kinematic chain.

* * * * *

UNITED STATES PATENT AND TRADEMARK OFFICE
CERTIFICATE OF CORRECTION

| | | |
|---|---|---|
| PATENT NO. | : 12,232,836 B2 | Page 1 of 1 |
| APPLICATION NO. | : 17/076755 | |
| DATED | : February 25, 2025 | |
| INVENTOR(S) | : Konrad Leibrandt | |

It is certified that error appears in the above-identified patent and that said Letters Patent is hereby corrected as shown below:

On the Title Page

Item (71) Applicant, delete "Redwood City, CA (US)" and insert --Santa Clara, CA (US)--

Signed and Sealed this
Twenty-second Day of April, 2025

Coke Morgan Stewart
*Acting Director of the United States Patent and Trademark Office*